(12) United States Patent
D'Elia et al.

(10) Patent No.: US 7,723,097 B2
(45) Date of Patent: May 25, 2010

(54) ESCHERICHIA COLI STRAINS THAT OVER-PRODUCE L-THREONINE AND PROCESSES FOR THEIR PRODUCTION

(75) Inventors: John N. D'Elia, Argenta, IL (US); Sean W. Jordan, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 568 days.

(21) Appl. No.: 11/371,732

(22) Filed: Mar. 9, 2006

(65) Prior Publication Data

US 2006/0205044 A1    Sep. 14, 2006

Related U.S. Application Data

(60) Provisional application No. 60/660,951, filed on Mar. 11, 2005.

(51) Int. Cl.
C12N 15/53 (2006.01)
C12N 15/63 (2006.01)
C12N 1/21 (2006.01)

(52) U.S. Cl. .............................. 435/252.33; 435/320.1; 435/189; 435/115

(58) Field of Classification Search ........................ None
See application file for complete search history.

(56) References Cited

U.S. PATENT DOCUMENTS

| | | | |
|---|---|---|---|
| 3,375,173 A | 3/1968 | Nishimura et al. | |
| 3,580,810 A | 5/1971 | Shiio et al. | |
| 4,321,325 A | 3/1982 | Debabov et al. | |
| 4,347,318 A | 8/1982 | Miwa et al. | |
| 4,371,615 A | 2/1983 | Miwa et al. | |
| 4,463,094 A | 7/1984 | Chibata et al. | |
| 4,601,983 A | 7/1986 | Nakamori et al. | |
| 4,757,009 A | 7/1988 | Sano et al. | |
| 4,945,058 A | 7/1990 | Yanai et al. | |
| 4,946,781 A | 8/1990 | Nakamori et al. | |
| 4,980,285 A | 12/1990 | Sano et al. | |
| 5,017,483 A | 5/1991 | Furukawa et al. | |
| 5,077,207 A | 12/1991 | Shiio et al. | |
| 5,087,566 A | 2/1992 | Takano et al. | |
| 5,098,835 A | 3/1992 | Yamada et al. | |
| 5,153,123 A | 10/1992 | Terasawa et al. | |
| 5,164,307 A | 11/1992 | Yoshihara et al. | |
| 5,175,107 A | 12/1992 | Debabov et al. | |
| 5,236,831 A | 8/1993 | Katsumata et al. | |
| 5,264,353 A | 11/1993 | Yamada et al. | |
| 5,474,918 A | 12/1995 | Kino et al. | |
| 5,939,307 A | 8/1999 | Wang et al. | |
| 6,451,564 B1 | 9/2002 | Guillouet et al. | |
| 6,455,284 B1 | 9/2002 | Gokarn et al. | |
| 6,630,332 B2 | 10/2003 | Rieping et al. | |
| 6,777,209 B1 | 8/2004 | Anderson et al. | |
| 7,186,531 B2 * | 3/2007 | Akhverdian et al. | ........ 435/106 |
| 2002/0106800 A1 | 8/2002 | Liaw et al. | |
| 2003/0017553 A1 | 1/2003 | Crafton et al. | |
| 2003/0055232 A1 * | 3/2003 | Li et al. | ...................... 536/23.1 |
| 2003/0059903 A1 | 3/2003 | Rieping et al. | |
| 2003/0113883 A1 | 6/2003 | Liaw et al. | |
| 2004/0126854 A1 | 7/2004 | Hanke et al. | |

FOREIGN PATENT DOCUMENTS

| | | |
|---|---|---|
| EP | 01408123 A1 | 4/2004 |
| WO | WO 02/081722 A2 | 10/2002 |
| WO | WO 03/008604 A2 | 1/2003 |
| WO | WO 03/008616 A2 | 1/2003 |
| WO | WO 03/038106 A2 | 5/2003 |
| WO | 2004/108894 | * 12/2004 |
| WO | WO 2005/054490 A1 | 6/2005 |

OTHER PUBLICATIONS

A.C. Looman et al. "Effects of heterologous ribosomal binding sites on the transcription and translation of the lacZ gene of *Escherichia coli*", Gene 37(1-3) 145-154. (1985).*

H.A. De Boer et al. "The tac Promoter: A Functional Hybrid Derived From the trp and lac Promoters", PNAS 80: 21-25 . (1983).*

Guillouet, S., et al., "Metabolic Redirection of Carbon Flow Toward Isoleucine by Expressing a Catabolic Threonine Dehydratase in a Threonine-Overproducing Corynebacterium Glutamicum," Appl. Microbiol Biotechnol (2001) 57:667-673.

Chassagnole, Christophe et al., "An Integrated Study of Threonine-Pathway Enzyme Kinetics in *Escherichia coli*", Biochem. J. (2001), 356, 415-423.

Raïs, Badr et al., "Threonine Synthesis from Aspartate in *Escherichia coli* Cell-Free Extracts: Pathway Dynamics", Biochem. J. (2001) 356, 425-432.

Boy, Emmanuelle, et al., "Multivalent Repression of Aspartic Semialdehyde Dehydrogenase in *Escherichia coli* K-12", Journal of Bacteriology, Oct. 1972, vol. 112(1), pp. 84-92.

Boy, Emmanuelle, "Role of Glucose-6-Phosphate in the Regulation of Aspartate Semialdehyde Dehydrogenase in *Escherichia coli*", FEMS Microbiology Letters 6(1979)189-192.

Haziza, Catherine, et al., "Nucleotide Sequence of the asd Gene of *Escherichia coli*: Absence of a Typical Attenuation Signal", EMBO Journal, vol. 1, No. 3, pp. 379-384, 1982.

Keseler, Ingrid M., et al., "EcoCyc: A Comprehensive Database Resource for *Escherichia coli*", Nucleic Acids Research, 2005, vol. 33, Database issue doi:10.1093/nar/gki108,0334-0337.

(Continued)

*Primary Examiner*—Rebecca E. Prouty
(74) *Attorney, Agent, or Firm*—Craig G. Cochenour; Duane A. Stewart, III; Buchanan Ingersoll & Rooney PC

(57) ABSTRACT

The invention relates to novel bacterial strains and constructs as well as methods for production of L-amino acids, including but not limited to L-threonine. Such novel bacterial strains may be characterized by, for instance, *Escherichia coli* strains in which an aspartate semialdehyde dehydrogenase (asd) gene is operably associated with at least one non-native promoter, non-native ribosome binding site, or both.

2 Claims, 8 Drawing Sheets

OTHER PUBLICATIONS

Haziza, Catherine, et al., "Identification of the promoter of the asd gene of *Escherichia coli* using in vitro fusion with the lac operon", Biochimie, 1982, 64, 227-230.

Oh, Min-Kyu et al., "Global Expression Profiling of Acetate-grown *Escherichia coli*", The Journal of Biological Chemistry, vol. 277, No. 15, Apr. 12, pp. 13175-13183, 2002.

Farmer, William R., et al. "Reduction of Aerobic Acetate Production by *Escherichia coli*", Applied Environmental Microbiology, Aug. 1997, p. 3205-3210, vol. 63, No. 8.

Ornston, L.N., et al., "Regulation of Glyoxylate Metabolism in *Escherichia coli* K-12", Journal of Bacteriology, Jun. 1969, p. 1098-1108, vol. 98, No. 3.

Resnik, Ernesto, et al., Integration Host Factor Amplifies the Induction of the aceBAK Operon of *Escherichia coli* by Relieving IcIR Repression, Journal of Bacteriology, May 1996, p. 2715-2717, vol. 178, No. 9.

Walsh, Kenneth, et al., "Determination of Flux Through the Branch Point of Two Metabolic Cycles", The Journal of Biological Chemistry, vol. 259, No. 15., Aug. 10, pp. 9646-9654.

Walsh, Kenneth, et al., "Branch Point Control by the Phosphorylation State of Isocitrate Dehydrogenase", The Journal of Biological Chemistry, vol. 260, No. 14, Jul. 15, pp. 8430-8437, 1985.

Ochman, Howard, "Neutral Mutations and Neutral Substitutions in Bacterial Genomes", Mol. Biol. Evol. 20(12):2091-2096, vol. 20, No. 12, 2003.

\* cited by examiner

Figure 2.

asd-tac-spc1 (5'-TTT TTC AT A AGC GTT TTT TTC CTG CAA AGA TGT GTG ACA ATT CCA CAC ATT ATA CGA GCC GAT GAT TAA TTG TCA ATG ACC TGA TAG TTT GGC TGT-3') (SEQ ID NO: 1)

asdUS-spc2 (5'-GCG ACT TTG GCT GCT TTT TGT ATG GTG AAA GAT GTG TAC AGT CTA TGC CTC GGG CA-3') (SEQ ID NO: 2)

asd-tac/trcrev2 (5'-GCG CCA GCC GAT AAA ACC AAC ATT TTT CAT AGCTGTTTCCTGTGTGAAATTGTTATCCGCTCAC AAT TCC ACA CAT TAT ACG-3') (SEQ ID NO: 3)

asd-trc-spc1 (5'-TTT TTC AT A AGC GTT TTT TTC CTG CAA AGA TGT GTG ACA ATT CCA CAC ATT ATA CGA GCC GGA TGA TTA ATT GTC AAT GAC CTG ATA GTT TGG CTG T-3') (SEQ ID NO: 4)

*Ptrc* (SEQ ID NO: 5)

TTGACAATTAATCATCCGGCTCGTATAATGTGTGGAATTGT

*Ptac* (SEQ ID NO: 6)

TTGACAATTAATCATCGGCTCGTATAATGTGTGGAATTGT

Figure 3.

*Ptac* with *asd* ribosome binding site (SEQ ID NO:7):

TTGACAATTAATCATCGGCTCGTATAATGTGTGGAATTGTCACACATCT
TTGCAGGAAAAAAACGCTT ATG

*Ptrc* with *asd* ribosome binding site (SEQ ID NO:8):

TTGACAATTAATCATCCGGCTCGTATAATGTGTGGAATTGTCACACAT
CTTTGCAGGAAAAAAACGCTT ATG

*Ptac* with *lac* ribosome binding site (SEQ ID NO:9):

TTGACAATTAATCATCGGCTCGTATAATGTGTGGAATTGTGAGCGGAT
AACAATTTCACACAGGAAACAGCT ATG

*Ptrc* with *lac* ribosome binding site (SEQ ID NO:10):

TTGACAATTAATCATCCGGCTCGTATAATGTGTGGAATTGTGAGCGGA
TAACAATTTCACACAGGAAACAGCT ATG

Constitutive *Ptac*-like promoter with *asd* ribosome binding site (in plasmid p4202-133-1) (SEQ ID NO: 11):   TTGACAATTAATCATCGGCT
CGTATAATGCACACATCTTTGCAGGAAAAAAACGCTT ATG

FIG. 4A

```
ATGAAAAATG TTGGTTTTAT CGGCTGGCGC GGTATGGTCG GCTCCGTTCT
CATGCAACGC ATGGTTGAAG AGCGCGACTT CGACGCCATT CGCCCTGTCT
TCTTTTCTAC TTCTCAGCTT GGCCAGGCTG CGCCGTCTTT TGGCGGAACC
ACTGGCACAC TTCAGGATGC CTTTGATCTG GAGGCGCTAA AGGCCCTCGA
TATCATTGTG ACCTGTCAGG GCGGCGATTA TACCAACGAA ATCTATCCAA
AGCTTCGTGA AAGCGGATGG CAAGGTTACT GGATTGACGC AGCATCGTCT
CTGCGCATGA AAGATGACGC CATCATCATT CTTGACCCCG TCAATCAGGA
CGTCATTACC GACGGATTAA ATAATGGCAT CAGGACTTTT GTTGGCGGTA
ACTGTACCGT AAGCCTGATG TTGATGTCGT TGGGTGGTTT ATTCGCCAAT
GATCTTGTTG ATTGGGTGTC CGTTGCAACC TACCAGGCCG CTTCCGGCGG
TGGTGCGCGA CATATGCGTG AGTTATTAAC CCAGATGGGC CATCTGTATG
GCCATGTGGC AGATGAACTC GCGACCCCGT CCTCTGCTAT TCTCGATATC
GAACGCAAAG TCACAACCTT AACCCGTAGC GGTGAGCTGC CGGTGGATAA
CTTTGGCGTG CCGCTGGCGG GTAGCCTGAT TCCGTGGATC GACAAACAGC
TCGATAACGG TCAGAGCCGC GAAGAGTGGA AAGGGCAGGC GGAAACCAAC
AAGATCCTCA ACACATCTTC CGTAATTCCG GTAGATGGTT TATGTGTGCG
TGTCGGGGCA TTGCGCTGCC ACAGCCAGGC ATTCACTATT AAATTGAAAA
AAGATGTGTC TATTCCGACC GTGGAAGAAC TGCTGGCTGC GCACAATCCG
TGGGCGAAAG TCGTTCCGAA CGATCGGGAA ATCACTATGC GTGAGCTAAC
CCCAGCTGCC GTTACCGGCA CGCTGACCAC GCCGGTAGGC CGCCTGCGTA
AGCTGAATAT GGGACCAGAG TTCCTGTCAG CCTTTACCGT GGGCGACCAG
```

FIG. 4B

CTGCTGTGGG GGGCCGCGGA GCCGCTGCGT CGGATGCTTC GTCAACTGGC

GTAA (SEQ ID NO: 12)

FIG. 5A

```
TCACCTGCCG GAAGCCCGCT GCTATTTCCT GAAGCGCTGG GGAAAATCAT
TTTAATGGCG ATCAGAAACA GAATGATGCC GCCAGAAATG GAGACGGTTT
CTGCTCGTAG GCTAAGAAAT GCCAGAATTT TCTCACCCGC AAACAGGAAC
ACCAGCATCA CCAGGAGAGC AATAAGCAAC TCTCGCACCA TGATTGCCCG
CCGTCTTTTC GGTTCAGTAT GTTTCAGTAC GGACATGAAA ATAGGTAGGT
TTCCGAGCGG ATCCATAATC AGGATCAATA AAACTGCTGC AGAAATGATT
TCATTCATAA CTCAAATTCC CTGATAATTG CCGCGGACTT TCTGCGTGCT
AACAAAGCAG GATAAGTCGC ATTACTGATG GCTTCGCTAT CATTGATTAA
TTTCACTTGC GACTTTGGCT GCTTTTGTA TGGTGAAAGA TGTGCCAAGA
GGAGACCGGC ACATTTATAC AGCACACATC TTTGCAGGAA AAAAACGCTT
ATGAAAAATG TTGGTTTTAT CGGCTGGCGC GGTATGGTCG GCTCCGTTCT
CATGCAACGC ATGGTTGAAG AGCGCGACTT CGACGCCATT CGCCCTGTCT
TCTTTTCTAC TTCTCAGCTT GGCCAGGCTG CGCCGTCTTT TGGCGGAACC
ACTGGCACAC TTCAGGATGC CTTTGATCTG GAGGCGCTAA AGGCCCTCGA
TATCATTGTG ACCTGTCAGG GCGGCGATTA TACCAACGAA ATCTATCCAA
AGCTTCGTGA AAGCGGATGG CAAGGTTACT GGATTGACGC AGCATCGTCT
CTGCGCATGA AAGATGACGC CATCATCATT CTTGACCCCG TCAATCAGGA
CGTCATTACC GACGGATTAA ATAATGGCAT CAGGACTTTT GTTGGCGGTA
ACTGTACCGT AAGCCTGATG TTGATGTCGT TGGGTGGTTT ATTCGCCAAT
GATCTTGTTG ATTGGGTGTC CGTTGCAACC TACCAGGCCG CTTCCGGCGG
TGGTGCGCGA CATATGCGTG AGTTATTAAC CCAGATGGGC CATCTGTATG
GCCATGTGGC AGATGAACTC GCGACCCCGT CCTCTGCTAT TCTCGATATC
```

FIG. 5B

```
GAACGCAAAG TCACAACCTT AACCCGTAGC GGTGAGCTGC CGGTGGATAA
CTTTGGCGTG CCGCTGGCGG GTAGCCTGAT TCCGTGGATC GACAAACAGC
TCGATAACGG TCAGAGCCGC GAAGAGTGGA AAGGGCAGGC GGAAACCAAC
AAGATCCTCA ACACATCTTC CGTAATTCCG GTAGATGGTT TATGTGTGCG
TGTCGGGGCA TTGCGCTGCC ACAGCCAGGC ATTCACTATT AAATTGAAAA
AAGATGTGTC TATTCCGACC GTGGAAGAAC TGCTGGCTGC GCACAATCCG
TGGGCGAAAG TCGTTCCGAA CGATCGGGAA ATCACTATGC GTGAGCTAAC
CCCAGCTGCC GTTACCGGCA CGCTGACCAC GCCGGTAGGC CGCCTGCGTA
AGCTGAATAT GGGACCAGAG TTCCTGTCAG CCTTTACCGT GGGCGACCAG
CTGCTGTGGG GGGCCGCGGA GCCGCTGCGT CGGATGCTTC GTCAACTGGC
GTAATCTTTA TTCATTAAAT CTGGGGCGCG ATGCCGCCCC TGTTAGTGCG
TAATACAGGA GTAAGCGCAG ATGTTTCATG ATTTACCGGG AGTTAAATAG
AGCATTGGCT ATTCTTTAAG GGTGGCTGAA TACATGAGTA TTCACAGCCT
TACCTGAAGT GAGGACGACG CAGAGAGGAT GCACAGAGTG CTGCGCCGTT
CAGGTCAAAA AAATGTCACA ACCAGAAGTC AAAAATCCAA TTGGATGGGG
TGACACAATA AAACAGGAAG ACAAGCATGT CCGATCGTAT CGATAGAGAC
GTGATTAACG CGCTAATTGC AGGCCATTTT GCGGATCCTT TTTCCGTACT
GGGAATGCAT AAAACCACCG CGGGACTGGA AGTCCGTGCC CTTTTACCCG
ACGCTACCGA TGTGTGGGTG ATTGAACCGA AAACCGGGCG CAAACTCGCA
AAACTGGAGT GTCTCGACTC ACGGGATTC TTTAGCGGCG TCATTCCGCG
ACGT
```

(SEQ ID NO: 13)

Figure 6.

tac-asd-for (5'- GCG GAA TTC GTG TTG ACA ATT AAT CAT CGG CTC GTA TAA TGC ACA CAT CTT GCA GGA AAA AAA CGC-3') (SEQ ID NO: 14)

tac-asd-rev (5'-CGC GGA TCC TTT TAT TGT GTC ACC CCA TCC AAT TGG-3') (SEQ ID NO: 15)

Constitutive *Ptac*-like promoter:

TTGACAATTAATCATCGGCTCGTATAATGC ACAC (SEQ ID NO: 16).

SEQUENCE LISTING

<160> NUMBER OF SEQ ID NOS: 16

<210> SEQ ID NO 1
<211> LENGTH: 96
<212> TYPE: DNA
<213> ORGANISM: Artificial Sequence
<220> FEATURE:
<223> OTHER INFORMATION: PCR Primer

<400> SEQUENCE: 1
tttttcataa gcgttttttt cctgcaaaga tgtgtgacaa ttccacacat tatacgagcc    60
gatgattaat tgtcaatgac ctgatagttt ggctgt                              96

<210> SEQ ID NO 2
<211> LENGTH: 56
<212> TYPE: DNA
<213> ORGANISM: Artificial Sequence
<220> FEATURE:
<223> OTHER INFORMATION: PCR Primer

<400> SEQUENCE: 2
gcgactttgg ctgcttttg tatggtgaaa gatgtgtaca gtctatgcct cgggca         56

<210> SEQ ID NO 3
<211> LENGTH: 82
<212> TYPE: DNA
<213> ORGANISM: Artificial Sequence
<220> FEATURE:
<223> OTHER INFORMATION: PCR Primer

<400> SEQUENCE: 3
gcgccagccg ataaaaccaa cattttcat agctgtttcc tgtgtgaaat tgttatccgc     60
tcacaattcc acacattata cg                                             82

<210> SEQ ID NO 4
<211> LENGTH: 97
<212> TYPE: DNA
<213> ORGANISM: Artificial Sequence

```
<220> FEATURE:
<223> OTHER INFORMATION: PCR Primer

<400> SEQUENCE: 4
tttttcataa gcgttttttt cctgcaaaga tgtgtgacaa ttccacacat tatacgagcc      60
ggatgattaa ttgtcaatga cctgatagtt tggctgt                              97

<210> SEQ ID NO 5
<211> LENGTH: 41
<212> TYPE: DNA
<213> ORGANISM: Artificial Sequence
<220> FEATURE:
<223> OTHER INFORMATION: artificial promoter

<400> SEQUENCE: 5
ttgacaatta atcatccggc tcgtataatg tgtggaattg t                         41

<210> SEQ ID NO 6
<211> LENGTH: 40
<212> TYPE: DNA
<213> ORGANISM: Artificial Sequence
<220> FEATURE:
<223> OTHER INFORMATION: artificial promoter

<400> SEQUENCE: 6
ttgacaatta atcatcggct cgtataatgt gtggaattgt                           40

<210> SEQ ID NO 7
<211> LENGTH: 71
<212> TYPE: DNA
<213> ORGANISM: Artificial Sequence
<220> FEATURE:
<223> OTHER INFORMATION: Promoter and RBS

<400> SEQUENCE: 7
ttgacaatta atcatcggct cgtataatgt gtggaattgt cacacatctt tgcaggaaaa     60
aaacgcttat g                                                         71

<210> SEQ ID NO 8
<211> LENGTH: 72
<212> TYPE: DNA
<213> ORGANISM: Artificial Sequence
<220> FEATURE:
<223> OTHER INFORMATION: Promoter and RBS

<400> SEQUENCE: 8
ttgacaatta atcatccggc tcgtataatg tgtggaattg tcacacatct tgcaggaaa      60 aaaacgctta tg                                                        72

<210> SEQ ID NO 9
<211> LENGTH: 75
<212> TYPE: DNA
<213> ORGANISM: Artificial Sequence
<220> FEATURE:
<223> OTHER INFORMATION: Promoter and RBS

<400> SEQUENCE: 9
ttgacaatta atcatcggct cgtataatgt gtggaattgt gagcggataa caatttcaca     60
caggaaacag ctatg                                                     75

<210> SEQ ID NO 10
<211> LENGTH: 76
<212> TYPE: DNA
```

<213> ORGANISM: Artificial Sequence
<220> FEATURE:
<223> OTHER INFORMATION: Promoter and RBS

<400> SEQUENCE: 10

```
ttgacaatta atcatccggc tcgtataatg tgtggaattg tgagcggata acaatttcac    60
acaggaaaca gctatg                                                   76
```

<210> SEQ ID NO 11
<211> LENGTH: 60
<212> TYPE: DNA
<213> ORGANISM: Artificial Sequence
<220> FEATURE:
<223> OTHER INFORMATION: inventor promoter fusion

<400> SEQUENCE: 11

```
ttgacaatta atcatcggct cgtataatgc acacatcttt gcaggaaaaa aacgcttatg    60
```

<210> SEQ ID NO 12
<211> LENGTH: 2104
<212> TYPE: DNA
<213> ORGANISM: Escherichia coli

<400> SEQUENCE: 12

```
tcacctgccg gaagcccgct gctatttcct gaagcgctgg ggaaaatcat tttaatggcg    60
atcagaaaca gaatgatgcc gccagaaatg agacggtttc tgctcgtag gctaagaaat    120 gccagaattt tctcacccgc aaacaggaac accagcatca ccaggagagc aataagcaac    180
tctcgcacca tgattgcccg ccgtcttttc ggttcagtat gtttcagtac ggacatgaaa    240
ataggtaggt ttccgagcgg atccataatc aggatcaata aaactgctgc agaaatgatt    300
tcattcataa ctcaaattcc ctgataattg ccgcggactt tctgcgtgct aacaaagcag    360
gataagtcgc attactgatg gcttcgctat cattgattaa tttcacttgc gactttggct    420 gcttttttgta tggtgaaaga tgtgccaaga ggagaccggc acatttatac agcacacatc    480
tttgcaggaa aaaacgcttt atgaaaaatg ttggttttat cggctggcgc ggtatggtcg    540
gctccgttct catgcaacgc atggttgaag agcgcgactt cgacgccatt cgccctgtct    600
tcttttctac ttctcagctt ggccaggctg cgccgtcttt tggcggaacc actggcacac    660
ttcaggatgc ctttgatctg gaggcgctaa aggccctcga tatcattgtg acctgtcagg    720
gcggcgatta taccaacgaa atctatccaa agcttcgtga aagcggatgg caaggttact    780
ggattgacgc agcatcgtct ctgcgcatga agatgacgc catcatcatt cttgaccccg    840
tcaatcagga cgtcattacc gacgattaa ataatggcat caggacttt gttggcggta    900 actgtaccgt aagcctgatg ttgatgtcgt tgggtggttt attcgccaat gatcttgttg    960
attgggtgtc cgttgcaacc taccaggccg cttccggcgg tggtgcgcga catatgcgtg    1020
agttattaac ccagatgggc catctgtatg ccatgtggc agatgaactc gcgacccgt    1080 cctctgctat tctcgatatc gaacgcaaag tcacaacctt aacccgtagc ggtgagctgc    1140
cggtggataa ctttggcgtg ccgctggcgg gtagcctgat tccgtggatc gacaaacagc    1200
tcgataacgg tcagagccgc gaagagtgga agggcaggc ggaaaccaac aagatcctca    1260
acacatcttc cgtaattccg gtagatggtt tatgtgtgcg tgtcgggca ttgcgctgcc    1320 acagccaggc attcactatt aaattgaaaa agatgtgtc tattccgacc gtggaagaac    1380
tgctggctgc gcacaatccg tgggcgaaag tcgttccgaa cgatcgggaa atcactatgc    1440
gtgagctaac cccagctgcc gttaccggca cgctgaccac gccggtaggc cgcctgcgta    1500
```

-continued

```
agctgaatat gggaccagag ttcctgtcag cctttaccgt gggcgaccag ctgctgtggg    1560
gggccgcgga gccgctgcgt cggatgcttc gtcaactggc gtaatcttta ttcattaaat    1620
ctggggcgcg atgccgcccc tgttagtgcg taatacagga gtaagcgcag atgtttcatg    1680
atttaccggg agttaaatag agcattggct attctttaag ggtggctgaa tacatgagta    1740
ttcacagcct tacctgaagt gaggacgacg cagagaggat gcacagagtg ctgcgccgtt    1800
caggtcaaaa aaatgtcaca accagaagtc aaaaatccaa ttggatgggg tgacacaata    1860
aaacaggaag acaagcatgt ccgatcgtat cgatagagac gtgattaacg cgctaattgc    1920
aggccatttt gcggatcctt tttccgtact gggaatgcat aaaaccaccg cgggactgga    1980
agtccgtgcc cttttacccg acgctaccga tgtgtgggtg attgaaccga aaaccgggcg    2040
caaactcgca aaactggagt gtctcgactc acggggattc tttagcggcg tcattccgcg    2100
acgt                                                                 2104

<210> SEQ ID NO 13
<211> LENGTH: 1994
<212> TYPE: DNA
<213> ORGANISM: Escherichia coli

<400> SEQUENCE: 13
acgtcgcgga atgacgccgc taaagaatcc ccgtgagtcg agacactcca gttttgcgag      60
tttgcgcccg gttttcggtt caatcaccca cacatcggta gcgtcgggta aagggcacg     120 gacttccagt cccgcggtgg ttttatgcat tcccagtacg gaaaaaggat ccgcaaaatg     180
gcctgcaatt agcgcgttaa tcacgtctct atcgatacga tcggacatgc ttgtcttcct     240
gttttattgt gtcaccccat ccaattggat ttttgacttc tggttgtgac atttttttga     300
cctgaacggc gcagcactct gtgcatcctc tctgcgtcgt cctcacttca ggtaaggctg     360
tgaatactca tgtattcagc cacccttaaa gaatagccaa tgctctattt aactcccggt     420
aaatcatgaa acatctgcgc ttactcctgt attacgcact aacaggggcg gcatcgcgcc     480
ccagatttaa tgaataaaga ttacgccagt tgacgaagca tccgacgcag cggctccgcg     540 gcccccccaca gcagctggtc gcccacggta aaggctgaca ggaactctgg cccacggatt     600
gtgcgcagcc agcagttctt ccacggtcgg aatagacaca tcttttttca atttaatagt     660
gaatgcctgg ctgtggcagc gcaatgcccc gacacgcaca cataaaccat ctaccggaat     720
tacggaagat gtgttgagga tcttgttggt ttccgcctgc cctttccact cttcgcggct     780
ctgaccgtta tcgagctgtt tgtcgatcca cggaatcagg ctacccgcca gcggcacgcc     840
aaagttatcc accggcagct caccgctacg ggttaaggtt gtgactttgc gttcgatatc     900
gagaatagca gaggacgggg tcgcgagttc atctgccaca tggccataca gatggcccat     960
ctgggttaat aactcacgca tatgtcgcgc accaccgccg gaagcggcct ggtaggttgc    1020
aacggacacc caatcaacaa gatcattggc gaataaacca cccaacgaca tcaacatcag    1080
gcttacggta cagttaccgc caacaaaagt cctgatgcca ttatttaatc cgtcggtaat    1140
gacgtcctga ttgacggggt caagaatgat gatggcgtca tctttcatgc gcagagacga    1200
tgctgcgtca atccagtaac cttgccatcc gctttcacga agctttggat agatttcgtt    1260
ggtataatcg ccgccctgac aggtcacaat gatatcgagg gcctttagcg cctccagatc    1320
aaaggcatcc tgaagtgtgc cagtggttcc gccaaaagac ggcgcagcct ggccaagctg    1380
agaagtagaa aagaagacag ggcgaatggc gtcgaagtcg cgctcttcaa ccatgcgttg    1440
```

```
catgagaacg gagccgacca taccgcgcca gccgataaaa ccaacatttt tcataagcgt    1500
ttttttcctg caaagatgtg tgctgtataa atgtgccggt ctcctcttgg cacatctttc    1560
accatacaaa aagcagccaa agtcgcaagt gaaattaatc aatgatagcg aagccatcag    1620
taatgcgact tatcctgctt tgttagcacg cagaaagtcc gcggcaatta tcagggaatt    1680
tgagttatga atgaaatcat ttctgcagca gttttattga tcctgattat ggatccgctc    1740
ggaaacctac ctattttcat gtccgtactg aaacatactg aaccgaaaag acggcgggca    1800
atcatggtgc gagagttgct tattgctctc ctggtgatgc tggtgttcct gtttgcgggt    1860
gagaaaattc tggcatttct tagcctacga gcagaaaccg tctccatttc tggcggcatc    1920
attctgtttc tgatcgccat taaaatgatt ttccccagcg cttcaggaaa tagcagcggg    1980
cttccggcag gtga                                                     1994

<210> SEQ ID NO 14
<211> LENGTH: 67
<212> TYPE: DNA
<213> ORGANISM: Artificial Sequence
<220> FEATURE:
<223> OTHER INFORMATION: PCR Primer

<400> SEQUENCE: 14
gcggaattcg tgttgacaat taatcatcgg ctcgtataat gcacacatct ttgcaggaaa    60
aaaacgc                                                             67

<210> SEQ ID NO 15
<211> LENGTH: 36
<212> TYPE: DNA
<213> ORGANISM: Artificial Sequence
<220> FEATURE:
<223> OTHER INFORMATION: PCR Primer

<400> SEQUENCE: 15
cgcggatcct tttattgtgt caccccatcc aattgg                              36

<210> SEQ ID NO 16
<211> LENGTH: 34
<212> TYPE: DNA
<213> ORGANISM: Artificial sequence
<220> FEATURE:
<223> OTHER INFORMATION: Artificial promoter

<400> SEQUENCE: 16
ttgacaatta atcatcggct cgtataatgc acac                                34
```

ESCHERICHIA COLI STRAINS THAT OVER-PRODUCE L-THREONINE AND PROCESSES FOR THEIR PRODUCTION

CLAIM TO PRIORITY

This application claims priority to pending U.S. Provisional Patent Application No. 60/660,951, having a filing date of Mar. 11, 2005. That application is incorporated by reference as if fully rewritten herein.

BACKGROUND

The following includes information that may be useful in understanding the present inventions. It is not an admission that any of the information provided herein is prior art, or material, to the presently described or claimed inventions, or that any publication or document that is specifically or implicitly referenced is prior art.

The present invention relates to, but is not limited to, the fields of microbiology and microbial genetics. The invention relates, for example, to novel bacterial strains, novel nucleotide sequences, novel amino acid sequences, and processes for employing these bacterial strains, novel nucleotide sequences, and/or novel amino acid sequences for fermentative production of amino acids including, but not limited to, L-threonine, L-methionine, L-lysine, L-homoserine, and L-isoleucine. Preferably L-threonine is produced. The invention also relates to the production of animal feed additives. The invention also relates to fermentation and synthesis of fine chemicals including but not limited to those listed above.

In *Escherichia coli*, the amino acids L-threonine, L-isoleucine, L-lysine and L-methionine derive all or part of their carbon atoms from aspartate (aspartic acid) via the following common biosynthetic pathway (G. N. Cohen, "The Common Pathway to Lysine, Methionine and Threonine," pp. 147-171 in *Amino Acids: Biosynthesis and Genetic Regulation*, K. M. Herrmann and R. L. Somerville, eds., Addison-Wesley Publishing Co., Inc., Reading, Mass. (1983)):

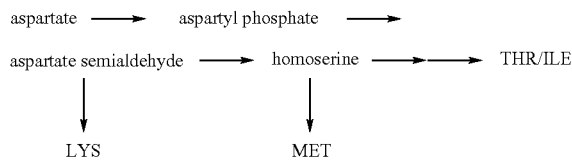

The first reaction of this common pathway is catalyzed by one of three distinct aspartate kinases (AK I, II, or III), each of which is encoded by a separate gene and differs from the others in the way its activity and synthesis are regulated.

Aspartate kinase I, for example, is encoded by thrA, its activity is inhibited by threonine, and its synthesis is repressed by threonine and isoleucine in combination. AK II, however, is encoded by metL and its synthesis repressed by methionine (although its activity is not inhibited by methionine or by paired combinations of methionine, lysine, threonine and isoleucine (F. Falcoz-Kelly et al., *Eur. J. Biochem.* 8:146-152 (1969); J. C. Patte et al., *Biochim. Biophys. Acta* 136:245-257 (1967)). AK III is encoded by lysC, and its activity and synthesis are inhibited and repressed, respectively, by lysine.

Aspartate semialdehyde dehydrogenase is encoded by the asd gene, and its activity is regulated through multivalent repression by lysine, threonine, and methionine (K. Haziza et al., *EMBO J.* 1(3):379-384 (1982)). Its synthesis is also reported to be regulated through repression by glucose-6-phosphate (G6P), and through metabolic regulation by guanosine 5'-diphosphate,3'-diphosphate. Aspartate semialdehyde dehydrogenase catalyzes conversion of L-aspartyl-4-P to L-aspartate-semialdehyde (Chassagnole et al., *Biochem. J.* 356:415-423 (2001)).

Map positions and nucleotide numbers for various genes in the *E. coli* strain K-12, as reported in Keseler, I. M., et al., Ecocyc: A Comprehensive Database Resource for *E. coli*, *Nucleic Acids Res.* 33:D334-7 (2005) are shown below. Of course, this information is provided as illustrative only, and should not be read to limit the claims unless explicitly stated therein.

| Gene | Start Nucleotide | End Nucleotide |
|------|------------------|----------------|
| asd  | 3,572,901        | 3,571,798      |
| thrA | 337              | 2,799          |
| thrB | 2801             | 3733           |
| thrC | 3734             | 5020           |
| metL | 4127858          | 4130290        |
| lysC | 4231256          | 4229907        |

Two of the AKs, I and II, are not reported to be distinct proteins, but rather a domain of a complex enzyme that includes homoserine dehydrogenase I or II, respectively, each of which catalyzes the reduction of aspartate semialdehyde to homoserine (P. Truffa-Bachi et al., *Eur. J. Biochem.* 5:73-80 (1968)). Homoserine dehydrogenase I (HD I) is also encoded by thrA; its synthesis is repressed by threonine plus isoleucine, and its activity is inhibited by threonine. Homoserine dehydrogenase II (HD II) is similarly encoded by metL, and its synthesis is repressed by methionine.

Threonine biosynthesis includes the following additional reactions:

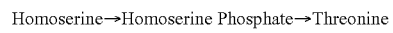

The phosphorylation of homoserine is catalyzed by homoserine kinase, a protein which is composed of two identical 29 kDa subunits encoded for by thrB and whose activity is inhibited by threonine (B. Burr et al., *J. Biochem.* 62:519-526 (1976)). The final step, the complex conversion of homoserine phosphate to L-threonine is catalyzed by threonine synthase, a 47 kDa protein encoded for by thrC (C. Parsot et al., *Nucleic Acids Res.* 11:7331-7345 (1983)).

Isoleucine can be produced in *E. coli* using threonine as a precursor (see Hashiguchi et al., *Biosci. Biotechnol. Biochem.* 63:672-679 (1999). More specifically, isoleucine is produced via the following reactions:

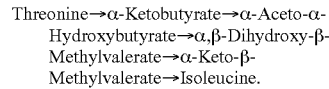

These reactions are said to be catalyzed in *E. coli*, respectively, by the following enzymes: threonine deaminase (ilvA); aceto-hydroxyacid synthetase I, II, or III (ilvBN, ilvGM, and ilvIH, respectively); dihydroxyacid reductoisomerase (ilvC); dihydroxyacid dehydratase (ilvD); and transaminase-B (ilvE).

The thrA, thrB and thrC genes all belong to the thr operon, a single operon located at 0 minutes on the genetic map of *E. coli* (J. Thze and I. Saint-Girons, *J. Bacteriol.* 118:990-998 (1974); J. Theze et al., *J. Bacteriol.* 117:133-143 (1974)). These genes encode, respectively, for aspartate kinase I, homoserine dehydrogenase I, homoserine kinase and threonine synthase. Biosynthesis of these enzymes is subject to multivalent repression by threonine and isoleucine (M. Freundlich, *Biochem. Biophys. Res. Commun.* 10:277-282 (1963)).

A regulatory region is found upstream of the first structural gene in the thr operon and its sequence has been reported (J. F. Gardner, *Proc. Natl. Acad. Sci. USA* 76:1706-1710 (1979)). A thr attenuator, downstream of the transcription initiation site, contains a sequence encoding a leader peptide; this sequence includes eight threonine codons and four isoleucine codons. The thr attenuator also contains the classical mutually exclusive secondary structures that permit or prevent RNA polymerase transcription of the structural genes in the thr operon, depending on the levels of the charged threonyl- and isoleucyl-tRNAs.

Because of the problems associated with obtaining high levels of amino acid production via natural biosynthesis (e.g., repression of the thr operon by the desired product), bacterial strains have been produced having plasmids containing a thr operon with a thrA gene that encodes a feedback-resistant enzyme. With such plasmids, L-threonine has been produced on an industrial scale by fermentation processes employing a wide variety of microorganisms, such as *Brevibacterium flavum*, *Serratia marcescens*, and *E. coli*.

For example, the *E. coli* strain BKIIM B-3996 (Debabov et al., U.S. Pat. No. 5,175,107), which contains the plasmid pVIC40, purportedly makes about 85 g/L in 36 hr. The host is a threonine-requiring strain because of a defective threonine synthase. In BKIIEM B-3996, it is the recombinant plasmid, pVIC40, that provides the crucial enzymatic activities, i.e., a feedback-resistant AK I-HD I, homoserine kinase and threonine synthase, needed for threonine biosynthesis. This plasmid also complements the host's threonine auxotrophy.

*E. coli* strain 29-4 (E. Shimizu et al., *Biosci. Biotech. Biochem.* 59:1095-1098 (1995)) is another reported example of a recombinant *E. coli* threonine producer. Strain 29-4 was constructed by cloning the thr operon of a threonine-over-producing mutant strain, *E. coli* K-12 (PIM-4) (derived from *E. coli* strain ATCC Deposit No. 21277), into plasmid pBR322, which was then introduced into the parent strain (K. Wiwa, et al., *Agric. Biol. Chem.* 47:2329-2334 (1983)). Strain 29-4 purportedly produces about 65 g/L of L-threonine in 72 hr.

Similarly constructed recombinant strains have been reported using other organisms. For example, the *Serratia marcescens* strain T2000 contains a plasmid having a thr operon that reportedly encodes a feedback-resistant thrA gene product and produces about 100 g/L of threonine in 96 hrs (M. Masuda et al., *Applied Biochem. Biotechn.* 37:255-262 (1992)). All of these strains are said to contain plasmids having multiple copies of the genes encoding the threonine biosynthetic enzymes, which allows over-expression of these enzymes. This over-expression of the plasmid-borne genes encoding threonine biosynthetic enzymes, particularly a thrA gene encoding a feedback-resistant AK I-HD I, reportedly enables these strains to produce large amounts of threonine. Other examples of plasmid-containing microorganisms are reported, for example, in U.S. Pat. Nos. 4,321,325; 4,347,318; 4,371,615; 4,601,983; 4,757,009; 4,945,058; 4,946,781; 4,980,285; 5,153,123; and 5,236,831.

Non-plasmid containing microorganisms have also been reported as threonine producers. Strains of *E. coli* such as H-8460, which is obtained by a series of conventional mutagenesis and selection for resistance to several metabolic analogs makes about 75 g/L of L-threonine in 70 hours (Kino, et al., U.S. Pat. No. 5,474,918). Strain H-8460 does not carry a recombinant plasmid and has one copy of the threonine biosynthetic genes on the chromosome. The lower productivity of this strain compared to the plasmid-bearing strains, such as BKIIM B-3996, is believed to be due to lower enzymatic activities (particularly those encoded by the thr operon) as these non-plasmid containing strains carry only a single copy of threonine biosynthetic genes.

An L-threonine producing strain of *E. coli*, KY10935, produced by multiple rounds of mutation, is reported in K. Okamoto, et al., *Biosci. Biotechnol. Biochem.* 61:1877-1882 (1997). When cultured under optimal conditions with DL-methionine, strain KY10935 is reported to produce as much as 100 g/liter L-threonine after 77 hours of cultivation. The level of L-threonine produced is believed to result from the inability of this strain to take up L-threonine that accumulates extracellularly, resulting in a decrease in the steady-state level of intracellular L-threonine and the release of the remaining regulatory steps in the L-threonine production pathway from feedback inhibition.

Other examples of non-plasmid containing microorganisms are reported, for example, in U.S. Pat. Nos. 5,939,307; 5,474,918; 5,264,353; 5,164,307; 5,098,835; 5,087,566; 5,077,207; 5,017,483; 4,463,094; 3,580,810; and 3,375,173.

Methods and techniques for the growth of bacterial cells, the introduction of isolated DNA molecules into host cells, and the isolation, cloning and sequencing of isolated nucleic acid molecules, etc., may generally be known to those of skill in the art. These methods and techniques are described in many standard laboratory manuals, such as Davis, et al., *Basic Methods In Molecular Biology* (1986), J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, et al., *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); P. F. Smith-Keary, Molecular Genetics of *Escherichia coli*, The Guilford Press, New York, N.Y. (1989); R. F. Schleif and P. C. Wensink, *Practical Methods in Molecular Biology*, Springer-Verlag (1981); M. Singer and P. Berg, Genes & Genomes, University Science Books, Mill Valley, Calif. (1991); P. B. Kaufman, et al., *Handbook of Molecular and Cellular Methods in Biology and Medicine*, CRC Press, Boca Raton, Fla. (1995); *Plasmids: A Practical Approach,* 2nd Edition, Hardy, K. D., ed., Oxford University Press, New York, N.Y. (1993); *Vectors. Essential Data*, Gacesa, P., and Ramji, D. P., eds., John Wiley & Sons Pub., New York, N.Y. (1994); *PCR primer: A Laboratory Manual*, Carl W. Dieffenbach and Gabriela S. Dveksler, eds. Cold Spring Harbor Laboratory Press, New York, N.Y. (1995); *PCR Protocols: A Guide to Methods and Applications*, Michael A. Innis, et al., eds. Academic Press, San Diego, Calif. (1990); *Guide to Electroporation and Electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of Plasmids*, Summers, D. K., Blackwell Science, Cambridge, Mass. (1996); *Understanding DNA and Gene Cloning. A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al., eds., Butterworth, Boston, Mass. (1988); *Bacterial Conjugation*, Clewell, D. B., ed., Plenum Press, New York, N.Y. (1993);

Del Solar, G., et al., Replication and control of circular bacterial plasmids, *Microbiol. Mol. Biol. Rev.* 62:434-464 (1998); Meijer, W. J., et al., Rolling-circle plasmids from *Bacillus subtilis*: complete nucleotide sequences and analyses of genes of pTA1015, pTA1040, pTA1050 and pTA1060, and comparisons with related plasmids from gram-positive bacteria, *FEMS Microbiol. Rev.* 21:337-368 (1998); Khan, S. A., Rolling-circle replication of bacterial plasmids, *Microbiol. Mol. Biol. Rev.* 61:442-455 (1997); Baker, R. L., Protein expression using ubiquitin fusion and cleavage, *Curr. Opin. Biotechnol.* 7:541-546 (1996); Makrides, S. C., Strategies for achieving high-level expression of genes in *Escherichia coli, Microbiol. Rev.* 60:512-538 (1996); Nicholl, D. S. T., *Introduction to Genetic Engineering* (2d ed.) 2002; Alonso, J. C., et al., Site-specific recombination in gram-positive theta-replicating plasmids, *FEMS Microbiol. Lett.* 142:1-10 (1996); Miroux, B., et al., Over-production of protein in *Escherichia coli*: mutant hosts that allow synthesis of some membrane protein and globular protein at high levels, *J. Mol. Biol.* 260: 289-298 (1996); Kurland, C. G., and Dong, H., Bacterial growth inhibited by overproduction of protein, *Mol. Microbiol.* 21:1-4 (1996); Saki, H., and Komano, T., DNA replication of IncQ broad-host-range plasmids in gram-negative bacteria, *Biosci. Biotechnol. Biochem.* 60:377-382 (1996); Deb, J. K., and Nath, N., Plasmids of *corynebacteria, FEMS Microbiol. Lett.* 175:11-20 (1999); Smith, G. P., Filamentous phages as cloning vectors, *Biotechnol.* 10:61-83 (1988); Espinosa, M., et al., Plasmid rolling circle replication and its control, *FEMS Microbiol. Lett.* 130:111-120 (1995); Lanka, E., and Wilkins, B. M., DNA processing reaction in bacterial conjugation, *Ann. Rev. Biochem.* 64:141-169 (!995); Dreiseikelmann, B., Translocation of DNA across bacterial membranes, *Microbiol. Rev.* 58:293-316 (1994); Nordstrom, K., and Wagner, E. G., Kinetic aspects of control of plasmid replication by antisense RNA, *Trends Biochem. Sci.* 19:294-300 (1994); Frost, L. S., et al., Analysis of the sequence gene products of the transfer region of the F sex factor, *Microbiol. Rev.* 58:162-210 (1994); Drury, L., Transformation of bacteria by electroporation, *Methods Mol. Biol.* 58:249-256 (1996); Dower, W. J., Electroporation of bacteria: a general approach to genetic transformation, *Genet. Eng.* 12:275-295 (1990); Na, S., et al., The factors affecting transformation efficiency of coryneform bacteria by electroporation, *Chin. J. Biotechnol.* 11: 193-198 (1995); Pansegrau, W., Covalent association of the traI gene product of plasmid RP4 with the 5'-terminal nucleotide at the relaxation nick site, *J. Biol. Chem.* 265:10637-10644 (1990); Bailey, J. E., Host-vector interactions in *Escherichia coli, Adv. Biochem. Eng. Biotechnol.* 48:29-52 (1993); Jane Dawson Funkhouser and W. Grady Smith, Monovalent Cation Effects on Lysine-sensitive Aspartokinase Catalytic Activity and Allosteric Regulation. *J. Biol. Chem.* (1974); Role of Glucose-6-phosphate in the regulation of aspartate semialdehyde dehydrogenase in *Escherichia coli. FEMS Microbiol. Letters* (1979); Multivalent repression of aspartic semialdehyde dehydrogenase in *Escherichia coli* K-12. *J. Bacteriol.* (1972); Christophe Chassagnole, et al., Control of threonine-synthesis pathway in *Escherichia coli*: a theoretical and experimental approach. *Biochem. J.* (2001); Badr Rais, Christophe Chassagnole, Thierry Letellier, David A. Fell, and Jean-Pierre Mazat, *Biochem. J.* (2001); *Escherichia coli* and *Salmonella* cellular and molecular biology, Neidhardt, et al, eds., American Society of Microbiology Press, Washington, D.C. (1996); Herman A. De Boer, et al., The tac promoter: a functional hybrid derived from the trp and lac promoters. *Proc. Natl. Acad. Sci.* (1983); Diane K. Hawley and William R. McClure, Compilation and analysis of *Escherichia coli* promoter DNA sequences. *Nucleic Acids Res.* (1983); Artem Khlebnikov and Jay D. Keasling, Effect of lacY expression on homogeneity of induction from the Ptac and Ptrc promoters by natural and synthetic inducers. *Biotechnol. Prog.* (2002); Martin E. Mulligan, et al., Characterization in vitro of the effect of spacer length on the activity of *Escherichia coli* RNA polymerase at the tac promoter. *J. Biol. Chem.* (1985); Jurgen Brosius, et al., Spacing of the −10 and −35 regions in the tac promoter. *J. Biol. Chem.* (1985); Peter Ruhdal Jensen and Karin Hammer, Artificial promoter for metabolic optimization. *Biotechnol. Bioengin.* (1998); Miroslav Patek, et al., Promoter from *Corynebacterium glutamicium*: cloning, molecular analysis and search for a consensus motif. *Microbiol.* (1996); J. Shine and L. Dalgarno, Determinant of cistron specificity in bacterial ribosome. Science (1975); J. Shine and L. Dalgarno, Terminal-sequence analysis of bacterial ribosomal RNA. Correlation between the 3'-terminal-polypyrimidine sequence of 16-S RNA and translational specificity of the ribosome. *Eur. J. Biochem.* (1975); Gary D. Stormo, et al. Characterization of translational initiation sites in *E. coli. Nucleic Acids Res.* (1982); H. A. De Boer, et al., A hybrid promoter and portable Shine-Dalgrano regions in *Escherichia coli. Biochem. Soc. Symp.* (1983); Peter Meinche, et al., Oligo kernels for data-mining on biological sequences: a case study on prokaryotic translation initiation sites. *BMC Bioinformatics* (2004); Doug Barrick, et al., Quantitative analysis of ribosome binding sites in *E. coli. Nucleic Acids Res.* (1994); Gila Lithwick and Hanah Margalit, Hierarchy of sequence-dependent features associated with prokaryotic translation. Genome Res. (2003); Jiong Ma, et al., Correlation between Shine-Dalgarno sequence and gene features such as predicted expression levels and operon structures. *J. Bacteriol.* (2002); Daisenko, K. A. and B. L. Wanner, One step inactivation of chromosomal genes in *Escherichia coli* K-12 using PCR products. *PNAS* 97:6640-6645 (2000); Alexeyev, M. F., et al. Improved antibiotic-resistance gene cassettes and omega elements for *Escherichia coli* vector construction and in vitro deletion/insertion mutagenesis. *Gene* 160:63-67 (1995); Cremer, J., et al., Regulation of enzymes of lysine Biosynthesis in *Corynebacterium glutamicum. J. Gen. Micro* 134:3221-3229 (1988); Haziza, C., et al., Identification of the promoter of the asd gene of *Escherichia coli* using in vitro fusion with the lac operon. *Biochimie* 64:227-230 (1982a); Haziza, C., et al., Nucleotide sequence of the asd gene of *Escherichia coli*: absence of a typical attenuation signal. *EMBO* 1:379-384 (1982b); Blattner, et al., The Complete genome sequence of *Escherichia coli* K-12. *Science* 277:1453-1474 (1997).

Although the applicants do not wish to be bound by any particular theory, it is believed that in both the non-plasmid and plasmid containing strains of *E. coli*, the thr operon is controlled by the particular strain's respective native threonine promoter. As described above, the expression of the native promoter is regulated by a mechanism controlled by a region of DNA that encodes a leader peptide and contains a number of threonine and isoleucine codons. This region is translated by a ribosome which senses the levels of threoninyl-tRNA and isoleucinyl-tRNA. When these levels are sufficient for the leader peptide to be translated, transcription is prematurely terminated, but when the levels are insufficient for the leader peptide to be translated, transcription is not terminated and the entire operon is transcribed, which, following translation, results in increased production of the threonine biosynthetic enzymes. Thus, when threonyl-tRNA and/or isoleucinyl-tRNA levels are low, the thr operon is maximally transcribed and the threonine biosynthetic enzymes are maximally made.

In the E. coli threonine-producing strain BKIIM B-3996, the threonine operon in the plasmid is controlled by its native promoter. As a result, the thr operon is only maximally expressed when the strain is starved for threonine and/or isoleucine. Since starvation for threonine is not possible in a threonine-producing strain, these strains have been rendered auxotrophic for isoleucine in order to obtain a higher level of enzymatic activity.

Another way of overcoming attenuation control is to lower the level(s) of threonyl-tRNA and/or isoleucinyl-tRNA in the cell. A thrS mutant, for example, having a threonyl-tRNA synthase which exhibits a 200-fold decreased apparent affinity for threonine, results in over-expression of the thr operon, presumably due to the low level of threonyl-tRNA (E. J. Johnson, et al., *J. Bacteriol.*, 129:66-70 (1977)).

In fermentation processes using these strains, however, the cells must be supplemented with isoleucine in the growth stage because of their deficient isoleucine biosynthesis. Subsequently, in the production stage, the cells are deprived of isoleucine to induce expression of the threonine biosynthetic enzymes. A major drawback, therefore, of using native threonine promoters to control expression of the threonine biosynthetic enzymes is that the cells must be supplemented with isoleucine.

E. coli strains have recently been reported that contain chromosomally integrated thr operons under the regulatory control of a non-native promoter (Wang, et al., U.S. Pat. No. 5,939,307, the entire disclosure of which is incorporated herein by reference). One of these strains, ADM Kat 13, was reported to produce as much as 102 g/L of L-threonine after 48 hours in culture. E. coli strains have also been reported that are produced by inserting in the chromosome of an E. coli cell at least one threonine operon operably linked to a non-native promoter to produce a parent strain, followed by performing at least one cycle of mutagenesis on the parent strain, followed by screening the mutagenized cells to identify E. Coli that produce specified amounts of L-threonine (United States Published Application No. US2002/0106800 A1, to Liaw et al.).

There remains a need in the art for microorganism strains that are culturable and produce amounts of amino acids such as threonine and isoleucine.

BRIEF SUMMARY

The inventions described and claimed herein have many attributes and encompass many embodiments including, but not limited to, those set forth in this Summary. The inventions described and claimed herein are not limited to or by the features or embodiments identified in this Summary, which is included for purposes of illustration only and not restriction.

One object of the invention is to provide microorganisms that efficiently produce an amino acid or amino acids (e.g. L-threonine, L-lysine, L-methionine, L-homoserine, and/or L-Isoleucine) in large amounts and/or high yields. In general, microorganisms of the invention do not have any unusual amino acid nutritional requirements, though one could of course design the microorganisms such that unusual nutritional requirements (including, for example, the requirement that an amino acid or amino acids be supplied) could exist.

In one aspect the invention includes a strain of the microorganism E. coli, wherein at least one chromosome of the strain contains at least one aspartate semialdehyde dehydrogenase (asd) gene operably associated with at least one non-native promoter, and the strain over-produces L-threonine, L-methionine, L-homoserine, L-isoleucine and/or L-lysine. The strain may over-produce L-threonine when compared to L-threonine production by a wild-type strain of E. coli, for example the E. coli strain K-12, and/or when compared to a parent strain.

In a further aspect of the invention, the strain of E. coli described above further comprises a non-native ribosome binding site operably associated with said asd gene and said non-native promoter. A non-native ribosome binding site may be selected from, for example, but is not limited to, a lac ribosome binding site, a thrA ribosome binding site, a folA ribosome binding site, an araC ribosome binding site, an araB ribosome binding site, a galE ribosome binding site, an ompA ribosome binding site, a trpE ribosome binding site, a lamB ribosome binding site, an MS2 coat ribosome binding site, and a Qβ coat ribosome binding site.

In one aspect of the invention, the non-native ribosome binding site used in the invention is selected from a strain of E. coli. For instance, the non-native ribosome binding site may be selected from E. coli strain TH25.79. References to ribosome binding sites may include but not be limited to consensus sequences, sequences found in nature, and mutated sequences.

A non-native promoter and/or a non-native ribosome binding site may be introduced, for example, by recombination or by mutagenesis of a native asd promoter or binding site.

In a yet further aspect of the invention, the previously discussed at least one non-native promoter may be selected from the group consisting of, for example, a tac promoter, a trc promoter, a lac promoter, a trp promoter, a lambda-$P_L$ promoter, a lambda-$P_R$ promoter, a lacUV5 promoter, an araBAD promoter, a lpp promoter, a constitutive Ptac-like promoter (SEQ ID NO: 16), and a lpp-lac promoter. References to promoters may include but not be limited to consensus sequences and mutated sequences.

In a further aspect of the invention, a strain of the invention may be less sensitive to regulation by lysine and other compounds than a wild-type strain of E. coli, and/or a parent strain of E. coli, for example less sensitive than the K-12 strain.

In further aspect of the invention includes a DNA construct comprising an aspartate semialdehyde dehydrogenase gene operably associated with at least one promoter heterologous to *Escherichia coli*. This DNA construct may further comprise at least one ribosome binding site operably associated with an asd gene and a promoter, wherein at least one ribosome binding site is not the E. coli asd ribosome binding site. The ribosome binding site may be, for example, but is not limited to, a lac operon ribosome binding site.

A DNA construct of the invention may be but is not limited to, for example, an extrachromosomal element. An extrachromosomal element may be for example, but is not limited to a vector. A vector of the invention may be, for example, but is not limited to a cosmid, plasmid, virus, phage, transposon, or minichromosome.

A DNA construct of the invention may include at least one promoter selected from, but not limited to, a trc promoter, a tac promoter, a trp promoter, a lac promoter, a lambda-$P_R$ promoter, a constitutive Ptac-like promoter (SEQ ID NO: 16), a lambda-$P_L$ promoter, a lacUV5 promoter, an araBAD promoter, a lpp promoter, and a lpp-lac promoter.

A further aspect of the invention includes a host cell comprising a DNA construct according to the invention. Such a host cell may be, for example, an E. coli cell. A host cell may be a cell that over-produces L-threonine, L-methionine, L-isoleucine, L-lysine, and/or L-homoserine. Preferably a host cell is a cell that overproduces L-threonine.

A yet still further aspect of the invention includes a process for producing L-threonine, comprising culturing an *E. coli* strain of the invention and/or a host cell of the invention in a culture medium.

In another aspect of the invention, a process for producing L-threonine using host cells and/or strains of the invention produces between about 40 and about 200 g/L of L-threonine in about 35 to about 60 hours of growth in culture; between about 60 and about 140 g/L of L-threonine in about 40 to about 55 hours of growth in culture; or between about 70 to about 100 g/L of L-threonine in about 45 to about 50 hours of growth in culture.

In a further aspect, the invention includes a strain of *E. coli* comprising an asd gene operably associated with a non-native promoter, where the asd gene product has a specific activity of between about 200 nmol/min/mg to about 30,000 nmol/min/mg.

In a yet still further aspect, the invention includes a strain of *E. coli* comprising an asd gene operably associated with a non-native promoter, where the asd gene product has a specific activity of between about 600 nmol/min/mg to about 9,000 nmol/min/mg.

Another aspect of the invention includes a method of making an *E. coli* cell that over-produces an amino acid, by selecting an *E. coli* parent cell that produces an amino acid in a given yield, then replacing a native asd promoter in the parent cell with a non-native promoter to produce an *E. coli* cell that produces the amino acid in a yield greater than the yield of the parent cell. This may also be accomplished by addition of a plasmid including at least one *E. coli* asd gene operably associated with a native and/or non-native promoter to a parent strain.

In a still further aspect, the invention includes the strains of *E. coli* selected from S4397-117-1, S4480-155-2, S4480-182-1, S4480-182-4, and TH25.79 including at least one copy of plasmid p4202-133-1. The invention may further include plasmid p4202-133-1.

In a further aspect, the invention may include a culture medium comprising a host cell and/or strain of the invention. The invention may also include a constitutive Ptac-like promoter (SEQ ID NO: 16).

BRIEF DESCRIPTION OF THE FIGURES

FIG. 1 depicts homologous recombination to exchange promoters used to express the asd gene. spcR=spectinomycin resistance cartridge, rightward facing arrows show approximate position of heterologous promoters (either Ptac or Ptrc). A linear PCR product (top line) containing spcR and a heterologous promoter are crossed into the chromosome (middle line) to yield strain with a heterologous promoter driving asd expression with a spectinomycin resistance immediately upstream of the heterologous promoter.

FIG. 2. FIG. 2 depicts the sequence of PCR primers used (SEQ ID NOs: 1-4, as shown). Bold residues provide sequence homology to asd allele and allow PCR product to be crossed into the chromosome via homologous recombination. Underlined residues encode promoter or a portion of a promoter (either Ptrc (SEQ ID NO: 5) or Ptac (SEQ ID NO: 6)). Boxed residues encode the start codon of asd.

FIG. 3. FIG. 3 shows the sequence of promoter regions of five different constructs with the start codon (ATG) boxed. Ptac with asd ribosome binding site as integrated in strain s4397-117-1 (SEQ ID NO:7). Ptrc with asd ribosome binding site as integrated in strain s4480-155-2 (SEQ ID NO:8). Ptac with lac ribosome binding site as integrated in strain s4480-182-1 (SEQ ID NO:9). Ptrc with lac ribosome binding site as integrated in strain s4480-182-4 (SEQ ID NO:10). Constitutive Ptac-like promoter with asd binding site as found in plasmid p4202-133-1, included in a TH25.79 host cell (SEQ ID NO: 11).

FIG. 4. FIG. 4 shows the nucleotide sequence of the asd gene of *E. coli* strain K-12 (SEQ ID NO: 12) as reported in Kessler, I. M., et al., *Nucleic Acids Res.* 33:D334-7 (2005).

FIG. 5. FIG. 5 shows the nucleotide sequence of the asd gene, as well as the preceeding 500 base pairs and succeeding 500 base pairs, of *E. coli* strain K-12 (SEQ ID NO: 13) as reported in Keseler, I. M., et al., *Nucleic Acids Res.* 33:D334-7 (2005).

FIG. 6. FIG. 6 shows the sequence of PCR primers used in Example 7 (SEQ ID NOS: 14-15, as shown). Bold and underlined sequences show restriction endonucleases sites. Bold sequences show linker and/or bases flanking the endonucleases sites. Underlined sequences show the residues of the Ptac promoter. Normal sequences show the where the PCR product is crossed into the chromosome via homologous recombination. A constitutive Ptac-like promoter of the invention is shown in SEQ ID NO: 16.

DETAILED DESCRIPTION

Figure 1:
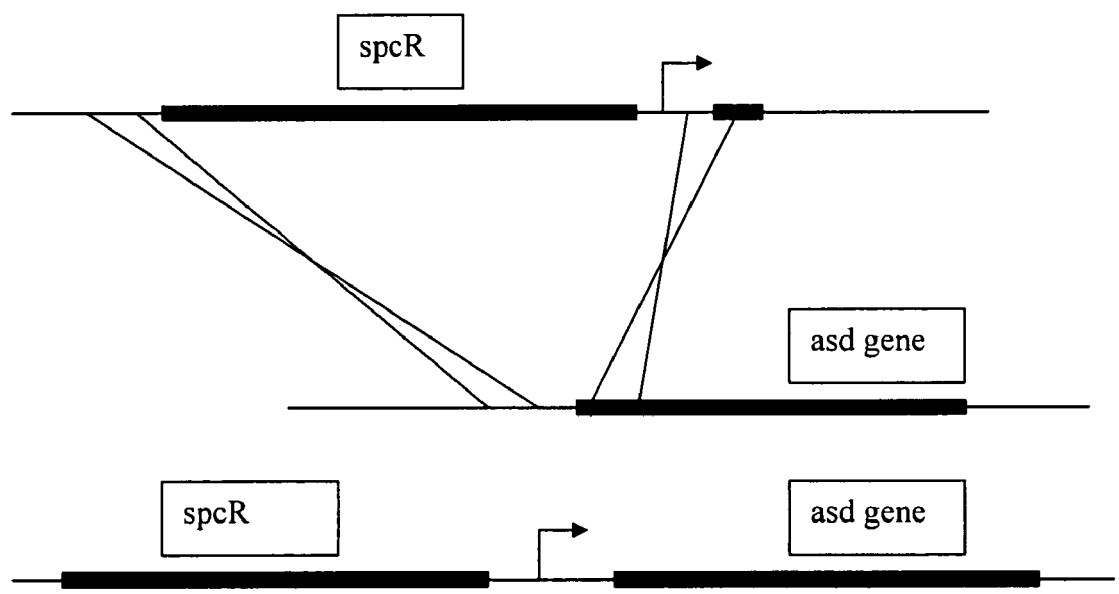
FIG. 1.

The present invention provides strains of novel microorganisms that, when grown in culture, produce relatively large amounts of amino acids, for example, L-threonine, L-lysine, L-homoserine, methionine and/or L-isoleucine. Also provided are methods for producing the strains and methods for use of the strains to produce amino acids, for example, L-threonine, L-lysine, L-homoserine, methionine and/or L-isoleucine.

I. Definitions

To provide a clear and consistent understanding of the specification and claims, including the scope to be given to terms therein, the following definitions are provided. Note that the term "a" or "an" entity refers to one or more of that entity; for example, "a polynucleotide" is understood to represent one or more polynucleotides. As such, the terms "a," "an," "one or more," and "at least one" can be used interchangeably herein.

Chromosomal Integration. As used herein, the term "chromosomal integration" refers to insertion of an exogenous DNA fragment into the chromosome of a host organism.

Constitutive. As used herein, the term "constitutive" refers to a promoter that is expressed and not known to be subject to regulation completely ceasing expression; that is, it is always "on."

Cosmid. As used herein, the term "cosmid" refers to a hybrid vector comprised of plasmid sequences and the cohesive ends of bacteriophage lambda.

Endogenous. As used herein, the term "endogenous" refers to a DNA sequence in an organism that is naturally occurring within that organism.

Exogenous. As used herein, the term "exogenous" refers to a DNA sequence in an organism that is not naturally occurring within that organism.

Extrachromosomal element. As used herein, the term "extrachromosomal element" refers to elements not associated with a chromosome. Extrachromosomal elements of the invention include, for example, but are not limited to, vectors. A vector may be, for example, but is not limited to a plasmid, cosmid, virus, phage, transposon or minichromosome.

Heterologous. As used herein, the term "heterologous" refers to structures from different sources, or having different evolutionary structure and/or function.

Homologous. As used herein, the term "homologous" refers to structures from the same source, or having the same evolutionary structure or function.

Homologous Recombination. As used herein, the term "homologous recombination" refers to the exchange of homologous or nearly homologous sequences between two DNA molecules.

Inducer. As used herein, the term "inducer" refers to a molecule that acts to stimulate transcription from an inducible promoter. The presence of an inducer (usually, but not always, an external molecule) stimulates transcription.

Isolated Polynucleotide. As used herein, the term "isolated polynucleotide" means a polynucleotide, DNA or RNA, that has been removed from its native environment. For example, recombinant DNA molecules contained in a vector are considered isolated. Further examples of isolated DNA molecules include recombinant DNA molecules maintained in heterologous host cells or purified (partially or substantially) DNA molecules in solution. A nucleic acid molecule contained in a clone that is a member of a mixed clone library and that has not been isolated from other clones of the library or a chromosome isolated or removed from a cell or a cell lysate, is not "isolated." Isolated RNA molecules include in vivo or in vitro RNA transcripts of DNA molecules included in the invention. Isolated DNA also includes DNA that is produced by PCR amplification.

Native promoter. As used herein, the term "native promoter" refers to a promoter that is an endogenous promoter operably associated with a gene in a parent strain.

Non-native promoter. As used herein, the term "non-native promoter" may refer to a promoter that is an endogenous promoter operably associated with a different gene than that with which it is operably associated in the microorganism as it is found in nature. A non-native promoter may also be a heterologous promoter.

A non-native promoter may also be a promoter that has had its sequence changed, deleted, replaced, and/or mutated with reference to a parent strain. Such change, deletion, replacement, and/or mutation may come about through any mechanism. Some possible mechanisms include but are not limited to chemical mutagenesis, ultraviolet mutagenesis, recombination, or other means as will be recognized by those skilled in the art. A non-native promoter may be created by one or more changes, deletions, replacements, or mutations. A non-native promoter may be created by multiple and/or successive mutations, changes, deletions, and/or replacements to a series of parental strains.

Operably associated. As used herein, the term "operably associated" refers to an associated of nucleic acid elements in a functional relationship. A nucleic acid is "operably associated" when it is placed into a functional relationship with another nucleic acid sequence. For instance, a promoter is operably associated with a polypeptide coding region if it affects the transcription of the polypeptide coding region. Operably associated nucleic acids are typically close together or contiguous and, where necessary, optimal, or useful, join two polypeptide coding regions, contiguous and in reading frame.

Operon. As used herein, the term "operon" refers to a contiguous portion of a transcriptional complex in which two or more open reading frames encoding polypeptides are transcribed as a multi-cistronic messenger RNA, controlled by a cis-acting promoter and possibly including other cis-acting sequences necessary for efficient transcription, as well as possibly including additional cis acting sequences important for efficient transcription and translation.

Over-produce. As used herein, the term "over-produce" refers to the production of a compound by a cell in an amount greater than the amount produced by a reference strain. A reference strain may be, for example, a parent strain used to produce a strain of the invention. A reference strain may also be a wild-type strain.

Parent strain. As used herein, the term "parent strain" refers to a strain of microorganism that is mutated, electroporated, or otherwise changed to provide a strain or host cell of the invention, or a strain that precedes a strain that has been mutated, electroporated, or otherwise changed to provide a strain or host cell of the invention.

Plasmid. As used herein, the term "plasmid" refers to a circular extrachromosomal element that may be used as a vector for cloning.

Promoter. As used herein, the term "promoter" refers to a portion of a gene containing DNA sequences that provide for binding of RNA polymerase and initiation of transcription and thus refers to a DNA sequence capable of controlling expression of a coding sequence or functional RNA. Promoter sequences are commonly, but not always, found in the 5' non-coding regions of genes, upstream of one or more open reading frames encoding polypeptides. Sequence elements within promoters that function in the initiation of transcription are often characterized by consensus nucleotide sequences. A promoter sequence may include both proximal and more distal upstream elements. Examples of proximal elements in bacterial promoters include a −10 region and a −35 region. A promoter may be, for example, constitutive, inducible, or environmentally responsive.

A promoter may be derived in its entirety from a native gene or may be a hybrid promoter. Hybrid promoters may be composed of different elements dereived from different promoters found in nature, and/or may comprise synthetic DNA segments.

Promoter, endogenous. As used herein, the term "endogenous promoter" refers to a promoter sequence that is a naturally occurring promoter sequence within the wild-type of a selected host microorganism.

Promoter, heterologous. As used herein, the term "heterologous promoter" refers to a promoter sequence that is a non-naturally occurring promoter sequence in a selected host microorganism. A non-naturally occurring promoter sequence may be from any prokaryotic or eukaryotic organism.

Promoter, synthetic. As used herein, the term "synthetic promoter" means a nucleotide sequence having promoter activity that is not known to be found in nature.

Regulation. As used herein, the term "regulation" refers to the rising and falling levels of some gene products in response to molecular signals. These gene products may be, for example, but are not limited to proteins and mRNA. Regulation may be "positive regulation," (or "induction") in which gene products increase under particular circumstances. Regulation may be "negative regulation," (or "repression") in which gene products decrease under particular circumstances.

Ribosome binding site (RBS). As used herein, the term "ribosome binding site" refers to a region of an mRNA molecule that binds a ribosome to initiate translation.

Ribosome binding site, non-native. As used herein, the term "non-native ribosome binding site" may refer to a ribosome binding site that is an endogenous ribosome binding site operably associated with a different gene than that with which it is operably associated in the microorganism as it is found in nature. A non-native ribosome binding site may also be a heterologous ribosome binding site. A non-native ribosome binding site may also be a ribosome binding site that has had its sequence changed, deleted, replaced, and/or mutated with reference to a parent strain. Such change, deletion, replacement, and/or mutation may come about through any mechanism. Some possible mechanisms include but are not limited to chemical mutagenesis, ultraviolet mutagenesis, recombination, or other means as will be recognized by those skilled in the art. A non-native ribosome binding site may be created by one or more changes, deletions, replacements, or mutations. A non-native ribosome binding site may be created by multiple and/or successive mutations, changes, deletions, and/or replacements to a series of parental strains.

Strain. As used herein, the term "strain" refers to bacteria of a particular species that have common characteristics. Unless indicated to the contrary, the terms "strain" and "cell" are used interchangeably herein.

Suppressor and Repressor. As used herein, the terms "suppressor" and "repressor" refer to molecules that act to block or reduce transcription from a derepressable promoter. A suppressor or repressor may be produced by a host cell and/or added to a medium in which a host cell is being grown or will be grown. During growth of a host cell a suppressor substance may be metabolized by the host cell, removing the host cell from culture medium and increasing transcription from the derepressable promoter.

Vector. As used herein, the term "vector" refers to a DNA molecule capable of replication in a host organism.

Yield. As used herein, the term "yield" refers to the amount of a product produced in relation to the amount of raw material consumed. With respect to amino acids produced by a microorganism, yield refers to the amount of amino acid produced with respect to the amount of raw material consumed by the process. For example, when 100 grams of dextrose is consumed by a microorganism that produces 25 grams of L-isoleucine, the yield of L-isoleucine, with respect to the dextrose, is 25%.

Unless otherwise indicated, all nucleotide sequences newly described herein were determined using an automated DNA sequencer (such as the Model 373 from Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. Those skilled in the art will recognize other ways in which one might check a DNA sequence.

II. Strains

Aspects of the invention include both methods of producing cells that over-produce an amino acid or amino acids as well as cells produced by those methods, descendants of those cells, and cells with similar characteristics. Although the invention is discussed herein in the context of the production of L-threonine, it is to be understood that methods, strains, and constructs of the invention may be used to produce other amino acids, including but not limited to L-methionine, L-isoleucine, and L-lysine.

Strains of the invention may include chromosomes and/or vectors including one or more asd genes, wherein at least one of the asd genes is operably associated with at least one promoter that is not a native asd promoter. Although applicants do not wish to be bound by any theory, it is believed that having an asd gene operably associated with a promoter that is not a native asd promoter will reduce or eliminate the regulation of the asd gene by the presence of lysine, which is believed to suppress production of aspartate semialdehyde dehydrogenase.

A non-native promoter with or without a non-native ribosome binding site may replace a native asd promoter and/or a native asd ribosome binding site, wherein the native asd promoter and/or native asd ribosome binding site is deleted, interrupted, or partially deleted and partially interrupted. For example, in strains S4397-117-1, S4480-155-2, S4480-182-1, and S4480-182-4, nucleotide sequences upstream of the transcriptional start site are derived entirely from the synthetic promoter and/or the synthetic RBS, with the native asd sequence beginning after the location of the start of transcription. By way of further example, plasmid p4202-133-1 includes a constitutive Ptac-like promoter, which includes the −10 region of the Ptac promoter, but nucleotides −1 through −5 (and, of course, others) when counted from the transcriptional start site are from the native asd promoter region. In a further aspect of the invention, the non-native promoter may be inserted in addition to a native promoter in the operon.

As will be recognized by those skilled in the art, one or more marker genes may be included in a chromosome and/or vector in addition to the non-native promoter. For example, a spectinomycin gene and a spectinomycin gene promoter may be inserted in a chromosome between the native promoter and the asd gene.

A number of promoters may be suitable for the invention. They include, for example, but are not limited to, the promoters tac, trc, lac, lpp, trp, lambda-$P_L$, lambda-$P_R$, lacUV5, araBAD, and lpp-lac. Exemplary nucleotide sequences for the promoters trc and tac are set forth in FIG. 2, and are SEQ ID NO:5 and SEQ ID NO:6, respectively.

A plasmid, chromosome or chromosomes of the strains of the invention may include more than one asd gene, and each gene may independently have either a non-native or native promoter operably associated with that gene. If there are more than one asd gene in a chromosome, they may include non-native promoters that are the same or different.

In addition to including a promoter that is not a native asd promoter operably associated with at least one asd gene, a strain of the invention may include a ribosome binding site operably associated with an asd gene and a non-native promoter, where the ribosome binding site is either a native asd ribosome binding site or a non-native ribosome binding site. Non-native ribosome binding sites for use in the invention include ribosome binding sites from lac, thrA, folA, araC, araB, galE, ompA, trpE, lamB, MS2 coat, and Qβ coat.

The native asd promoter in wild-type E. coli is said to be susceptible to regulation by lysine. In one aspect of the invention, a non-native promoter and/or non-native ribosome binding site is selected to decrease or eliminate lysine regulation of asd in a strain of the invention relative to a parent E. coli strain.

It should be understood that throughout this disclosure, nucleotide sequences and/or promoters disclosed in this invention should be construed to include both the consensus sequences for those sequences and/or promoters, and, in some aspects of the invention, nucleotide sequences that are at least 90%, 91%, 92%, 93%, 94%, 95%, 96%, 97%, 98%, 99%, or 100% identical to a disclosed sequence. Unless explicitly stated in the claims, it is not the intention of the inventors to be bound to a particular nucleotide sequence; those skilled in the art will recognize that some variation is both possible and customary within the above parameters, particularly but not limited to variation among strains in different laboratories or other environments.

As a practical matter, whether any particular nucleotide sequence is at least 90%, 91%, 92%, 93%, 94%, 95%, 96%, 97%, 98%, 99%, or 100% identical to a nucleotide sequence or complementary nucleotide sequence can be determined conventionally using sequence analysis computer programs such as OMIGA® Version 2.0 for Windows, available from Oxford Molecular, Ltd. (Oxford, U.K.) or the GCG® Wisconsin Package®. OMIGA® uses the CLUSTAL W alignment algorithm using the slow full dynamic programming alignment method with default parameters of an open gap penalty of 10 and an extend gap penalty of 5.0, to find the best alignment between two nucleotide sequences. When using CLUSTAL W or another sequence alignment program to determine whether a particular sequence is, for instance, 95% identical to a reference sequence, the parameters may be set such that the percentage of identity is calculated over the full length of the reference nucleotide sequence such that gaps, mismatches, or insertions of up to 5% of the total number of nucleotides in the reference sequence are allowed. Other sequence analysis methods and programs as known in the art may be used in the invention.

Experiments described in this disclosure used the GCG® Wisconsin Package® (Wisconsin Package Version 10.3, Accelrys Inc., San Diego, Calif. Portions of SeqLAb are based on the "Genetic Data Environment (GDE)", originally developed in the Department of Microbiology, University of Illinois, Urbana-Champaign, Ill., USA, and licensed to GCG), a sequencing program available from Accelrys®. Elements of the Wisconsin Package® that were used include GAP, SSEARCH, FASTA, and BLAST.

Gap considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Gap uses the alignment method of Needleman and Wunsch (*J. Mol. Biol.* 48; 443-453 (1970)) that has been shown to be equivalent to Sellers, SIAM, *J. of Applied Math* 26; 787-793 (1974)).

SSearch uses William Pearson's implementation of the method of Smith and Waterman, *Advances in Applied Mathematics* 2; 482-489 (1981), to search for similarities between one sequence (the query) and any group of sequences of the same type (nucleic acid or protein) as the query sequence.

FastA uses the method of Pearson and Lipman, *Proc. Natl. Acad. Sci. USA* 85; 2444-2448 (1988)) to search for similarities between one sequence (the query) and any group of sequences of the same type (nucleic acid or protein) as the query sequence.

In the first step of this search, the comparison can be viewed as a set of dot plots, with the query as the vertical sequence and the group of sequences to which the query is being compared as the different horizontal sequences. This first step finds the registers of comparison (diagonals) having the largest number of short perfect matches (words) for each comparison. In the second step, these "best" regions are rescored using a scoring matrix that allows conservative replacements, ambiguity symbols, and runs of identities shorter than the size of a word. In the third step, the program checks to see if some of these initial highest-scoring diagonals can be joined together. Finally, the search set sequences with the highest scores are aligned to the query sequence for display.

A FastA word is any short sequence (n-mer or k-tuple) where one has set n to some small integer less than or equal to six. For example, the word GGATGG is one of the 4,096 possible words of length six that can be created from an alphabet consisting of the four letters G, A, T, and C. By way of further example, the word QL is one of the 400 possible words of length two that one can make with the 20 letters of the amino acid alphabet.

BLAST, or Basic Local Alignment Search Tool, uses the method of Altschul, et al. (*J. Mol. Biol.* 215: 403-410 (1990)) to search for similarities between a query sequence and all the sequences in a database.

The release of BLAST used in deducting sequences as described herein implements version 2 of BLAST from the National Center for Biotechnology Information (NCBI) described in Altschul, et al. *Nucleic Acids Res.* 25(17): 3389-3402 (1997). BLAST is known as "gapped BLAST" because, in addition to offering a three-fold speedup over the original BLAST, it generates gapped alignments between query and database sequences.

III. DNA Constructs

In another aspect, the invention includes DNA constructs (e.g. extrachromosomal elements) that comprise at least a portion of an asd operon, for instance an asd gene, or for instance an *E. coli* asd gene operably associated with at least one promoter that is not the native asd promoter. DNA constructs of the invention may further include a ribosome binding site that is not the native *E. coli* asd gene ribosome binding site, for instance the lac ribosome binding site. Of course, DNA constructs of the invention may include other elements known to those in the art.

DNA constructs of the invention may be a vector or vectors. Vectors of the invention may comprise at least one regulatory element. For example, a regulatory element may be a promoter, operator, activator, and/or repressor. Vectors may also comprise an initiation sequence or sequences and/or a ribosome binding site or ribosome binding sites. Vectors may further comprise a selectable marker. Regulatory elements may be located on chromosomes of host cells and/or within other vectors.

DNA used for chromosomal integration as described in the invention may be generated, for example, using PCR (the polymerase chain reaction). PCR processes are set forth, for example, in U.S. Pat. Nos. 4,683,202, 4,683,195, 4,965,188, all of which are incorporated by reference herein.

Vectors of the invention may be, but are not limited to, a virus, a phage, a cosmid, a plasmid, a transposon, or a minichromosome. In a further aspect of the invention, a promoter operably associated with an asd gene in a DNA construct may be, for example, but is not limited to, tac, trc, lac, trp, lambda-$P_L$, lambda-$P_R$, lacUV5, araBAD, lpp, and lpp-lac.

In a further aspect of the invention, a host cell is provided that includes a DNA construct of the invention. A host cell may be a microorganism, including, for example, an *E. coli* cell, and may include further modifications or inclusions as will be recognized those skilled in the art. The host cell may produce at least one of L-threonine, L-isoleucine, L-lysine, L-methionine, and/or L-homoserine. In one aspect, the host cell produces at least one of L-threonine, L-lysine, L-methionine, L-isoleucine, and/or L-homoserine in higher yield than a wild-type host cell that does not bear at least one DNA construct of the invention.

IV. Culture Media and Processes for Amino Acid Production

The invention is also directed to use of the above-described and below-claimed strains and host cells in fermentation processes for production of amino acids in general. Such amino acids may include, for example, amino acids of the asparate family. Amino acids of the aspartate family may include, for example, L-threonine, L-methionine, L-isoleucine, L-homoserine and L-lysine. Amino acids may be obtained, for example, by culturing strains or host cells of the invention in a synthetic or natural medium containing at least one carbon source, at least one nitrogen source, and, as appropriate, inorganic salts, growth factors, and the like.

Examples of suitable carbon sources include but are not limited to carbohydrates, such as dextrose, fructose, starch, sucrose, starch hydrolysate, cellulose hydrolysate and molasses; organic acids, such as acetic acid, propionic acid, formic acid, malic acid, citric acid, and fumaric acid; and alcohols, such as glycerol and ethanol.

Examples of suitable nitrogen sources include but are not limited to ammonia, including ammonia gas and aqueous ammonia; ammonium salts of inorganic or organic acids, such as ammonium chloride, ammomium phosphate, ammonium sulfate, and ammonium acetate; and other nitrogen-containing substances, including meat extract, peptone, corn steep liquor, casein hydrolysate, soybean cake hydrolysate and yeast extract.

Culture media suitable for use with the invention includes but is not limited to the following media:

1. Minimal Medium. Davis minimal media (per 1 liter 7.0 g dipotassium phosphate, 2.0 g monopotassium phospate, 0.5 g/l sodium citrate, 0.1 magnesium sulfate, 1.0 g ammonium sulfate, pH 7.0 supplemented with a carbon source (typically dextrose) to 0.1% (w/v) and supplemented as needed with a source of amino acids (typically 0.1% casamino acids (w/v) or 0.15% yeast extract (w/v)).

2. SM2 (24.36 g/l $K_2HPO_4$, 9.52 g/l KH2PO4, 15 g/l yeast extract, 5 g/l $(NH_4)_2SO_4$, 32.5 g/l dextrose, 1.0 µl MgSO4-7H2O pH 7.2).

3. BTC3 (1.0 g/l K2HPO4, 10.0 g/l (NH4)2SO4, 40.8 g/l Bis-Tris, 20 ml/l 50% solids corn steep liquor (Sigma), 25.0 g/l dextrose, and 1.2 g/l $MgSO_4$-$7H_2O$ pH 7.0 supplemented as needed with amino acids source (typically 1.0% casamino acids or 1.5% yeast extract (w/v)).

Amino acids may be commercially produced using strains of the invention in, for example, batch type or fed-batch type fermentation processes. In batch type fermentations, nutrients are added at the beginning of the fermentation. In fed-batch or extended fed-batch type fermentations one or more nutrients are supplied (1) continuously to the culture, (2) from the beginning of the fermentation or after the culture has reached a certain age, and/or (3) when the nutrient(s) that are fed are exhausted from the culture medium.

A variation of the extended batch of fed-batch type fermentation is the repeated fed-batch or fill-and-draw fermentation, where part of the contents of the fermentor may be removed at a particular time (e.g., when the fermentor is full) while feeding of a nutrient is continued. In this way a fermentation can be extended for a longer time as compared to when such methods are not used.

Another type of fermentation, continuous fermentation or chemostat culture, uses continuous feeding of a complete medium while culture fluid is continuously or semi-continuously withdrawn in such a way that the volume of the broth in the fermentor remains approximately constant. A continuous fermentation can in theory be maintained for an infinite period of time.

In a batch fermentation, the cultured organism grows until either one of the essential nutrients in the medium becomes exhausted or fermentation conditions become unfavorable (e.g., the pH decreases to a value inhibitory for microbial growth). In fed-batch fermentations measures are normally taken to maintain favorable growth conditions (e.g., by using pH control) and exhaustion of one or more essential nutrients is prevented by feeding these nutrient(s) to the culture. Cultured microorganism will normally continue to grow at a rate determined by the rate of nutrient feed.

In some instances a single nutrient, very often a carbon source, will become limiting for growth. The same principle applies during continuous fermentation, in which one nutrient in the medium feed may be limiting and all of the other nutrients are in excess. After the microorganisms have stopped growing, the limiting nutrient will generally be present in the culture fluid in an extremely low concentration.

While different types of nutrient limitation can be employed, carbon source limitation is used most often. Other examples are limiting nutrients include the nitrogen, sulfur, phosphorous, trace metal, and oxygen sources. Vitamins and amino acid may also be limiting nutrients, particularly where a microorganism being cultured is auxotrophic for a limiting amino acid or vitamin.

After cultivation, amino acids (e.g., L-threonine, L-methionine, L-homoserine, L-lysine, and/or L-isoleucine) that have accumulated in the culture broth may be separated according to one or more of a variety of methods. For example, ion-exchange resins according to purify L-threonine according to methods described in U.S. Pat. No. 5,342,766. This method involves first removing the microorganisms from the culture broth by centrifugation and then adjusting the pH of the broth to about 2 using hydrochloric acid. The acidified solution is subsequently passed through a strongly acidic cation exchange resin and the adsorbent eluted using dilute aqueous ammonia. The ammonia is removed by evaporation under vacuum, and the resulting solution is condensed. Addition of alcohol and subsequent cooling provides crystals of L-threonine. A similar method for the purification of L-isoleucine from culture media is described in U.S. Pat. No. 5,474,918.

VI. Examples

The examples below are only representative of some aspects of the invention. It will be understood by those skilled in the art that the invention as set forth in the specification can be practiced with a variety of microorganisms and promoters. These examples and the strains used therein should not be interpreted as limiting the invention in any way not explicitly stated in the claims.

Example 1

Example 1 describes the production of strains with Ptac or Ptrc promoters inserted immediately upstream of the asd gene of *Escherichia coli* positioned in a manner that causes the constitutive high expression level of the asd gene product.

Ptac and Ptrc promoters (De Boer, et al, 1983; Brosius et al., 1985; and FIG. 3) were inserted upstream of the wild-type asd gene by transformation of strain TH25.79 with linear DNA encoding the streptomycin resistance gene from plasmid pBSL 175 (Alexeyev et al., 1995) (FIG. 1). Plasmid pBSL175 was used as template in a polymerase chain reaction (PCR) using primers asdUS-spc2 (SEQ ID NO: 2) (FIG. 2) and asd-tac-spc1 (SEQ ID NO: 1) (FIG. 2) (for insertion of the Ptac promoter) or asd-trc-spc1 (SEQ ID NO: 4) (FIG. 2) (for insertion of the Ptrc promoter). These PCR products contained the streptomycin resistance gene flanked by sequence homologous to that of the asd allele of strain TH25.79 and with the Ptac or Ptrc promoter substituted for the Pasd promoter (Haziza et al., 1982a). The PCR was performed using Advantage HF™ PCR kits (Clontech) following the manufacturer's directions. 50 ul reactions included 5 ul of 10×HF PCR reaction buffer (Clontech proprietary formula), 5 ul 10×HF dNTP mix (Clontech proprietary formula), 1 ul 50× Advantage-HF polymerase mix (which is composed of 50% glycerol, 40 mM Tris-HCL (pH 7.5), 50 mM KCl, 25 mM $(NH_4)_2SO4$, 1 mM EDTA, 5 mM 2-mercaptoethanol, 0.25% Thesit, 1.1 ug/ul TaqStart antibody, a Clontech proprietary amount of KlenTaq-1 DNA polymerase, and a Clontech proprietary amount of Deep Vent™ DNA polymerase), 0.5 ul of each primer (100 pmol/ul) and 1 ul of template DNA (1-50 pg/ul). Cycling was performed in an Applied Biosystems 9700 thermocycler as follows: pretreatment at 94° C. for 4 min then 25 cycles of 10 sec at 94° C., 30 sec at 55° C. and 90 sec at 68° C.

The PCR products were then used to transform strain TH25.79 carrying plasmid pKD46 following protocols previously described (Datsenko and Wanner, 2000) with the following modifications: 50 ml LB (Difco) cultures (in 250 ml baffled shake flasks) of strain s4370-69-2 carrying plasmid pKD46 growing at 30° C. on an orbital shaker were grown to an $OD_{600}$ of 0.4. 0.5 ml of 20% (w/v) arabinose was then added and the cultures were allowed to grow another 2.0 hours after which time electrocompetent cells were prepared by following the procedure of Datsenko and Wanner (2000).

Electroporation was performed by suspending 1.0-3.0 ug of precipitated PCR product in 45 µl of electrocompetent cells and transferring the mixture to a 0.1 cm electroporation cuvette. The cuvette was then pulsed in a Bio-Rad Gene Pulser® II at 1.8 kV, 25 µF, and 200Ω. The cells were then grown out in 1 ml 2YT (Difco) for 4 hours at 37° C. and the entire 1 ml was plated onto LB agar with 7.5 µg/ml spectinomycin and incubated at 37° C. for a period of 2-3 days.

Resultant spectinomycin resistant strains were cured of plasmid pKD46 as described in Datsenko and Wanner (2000), yielding strains s4397-117-1 (with Ptac driving Asd expression (SEQ ID NO: 7)), and s4480-155-2 (with Ptrc driving Asd expression (SEQ ID NO: 8)).

Example 2

Example 2 describes the production of strains with the constitutive high expression of the asd gene product controlled either by promoter Ptac and the lac ribosomal binding site from *Escherichia coli* or by Ptrc and the lac ribosomal binding site from *Escherichia coli*.

Substitution of the native asd ribosomal binding site (Haziza et al., 1982b) with the ribosomal binding site of the lac operon of *Escherichia coli* (Looman et al., 1985) was accomplished by transformation of linear DNA encoding the streptomycin resistance gene from plasmid pBSL175 (Alexeyev et al., 1995). The linear DNA was produced by PCR using primers asdUS-spc2 (SEQ ID NO: 2) (FIG. 2) and asd-tac/trcrev2 (SEQ ID NO: 3) (FIG. 2) with chromosomal DNA from strain s4397-117-1 (Table 1) or strain s4480-155-2 (Table 1) as template.

TABLE 1

| Strain | Promoter | Ribosome binding site | Primers | Template |
|---|---|---|---|---|
| S4397-117-1 | Ptac | asd | asd-tac-spc1 (SEQ ID NO: 1) & asdUS-spc2 (SEQ ID NO: 2) | pBSL175 |
| S4480-155-2 | Ptrc | asd | asd-trc-spc1 (SEQ ID NO: 4) & asdUS-spc2 (SEQ ID NO: 2) | pBSL175 |
| S4480-182-1 | Ptac | lac | asd-tac/trcrev2 (SEQ ID NO: 3) & asdUS-spc2 (SEQ ID NO: 2) | S4397-117-1 chromosome |
| S4480-182-4 | Ptrc | lac | asd-tac/trcrev2 (SEQ ID NO: 3) & asdUS-spc2 (SEQ ID NO: 2) | S4480-155-2 chromosome |
| TH25.79 | Pasd | asd | | |

Table 1. Construction of four different promoter-asd fusions in the wild-type strain TH25.79 showing promoter used, ribosomal binding site source, and primers and templates used to make PCR products used in transformation of linear DNA.

These PCR products encoded the streptomycin resistance gene flanked by DNA homologous to the asd allele (Blattner et al., 1997) of strain TH25.79 and include either the Ptac (SEQ ID NO: 6) (De Boer et al., 1983 and FIG. 3) or the Ptrc (SEQ ID NO: 5) (Brosius et al., 1985 and FIG. 3) promoter along with the ribosomal binding site from the lac operon substituted for the asd ribosomal binding site. The PCR was performed using Advantage HF™ PCR kits (Clontech) following the manufacturer's directions. 50 ul reactions included 5 ul of 10×HF PCR reaction buffer (Clontech proprietary formula), 5 ul 10×HF dNTP mix (Clontech proprietary formula), 1 ul 50× Advantage-HF polymerase mix (which is composed of 50% glycerol, 40 mM Tris-HCL (pH 7.5), 50 mM KCl, 25 mM $(NH_4)_2SO4$, 1 mM EDTA, 5 mM 2-mercaptoethanol, 0.25% Thesit, 1.1 ug/ul TaqStart antibody, a Clontech proprietary amount of KlenTaq-1 DNA polymerase, and a Clontech proprietary amount of Deep Vent™ DNA polymerase), 0.5 ul of each primer (100 pmol/ul) and 1 ul of template DNA (1-50 pg/ul) Cycling was performed in an Applied Biosystems 9700 thermocycler as follows: pretreatment at 94° C. for 4 min then 25 cycles of 10 sec at 94° C., 30 sec at 55° C. and 90 sec at 68° C.

The PCR products were then used to transform strain TH25.79 carrying plasmid pKD46 following protocols previously described (Datsenko and Wanner, 2000) with the following modifications: 50 ml LB (Difco) cultures (in 250 ml baffled shake flasks) of strain s4370-69-2 carrying plasmid pKD46 growing at 30° C. on an orbital shaker were grown to an $OD_{600}$ of 0.4. 0.5 ml of 20% (w/v) arabinose was then added and the cultures were allowed to grow another 2.0 hours after which time electrocompetent cells were prepared following the procedure of Datsenko and Wanner (2000).

Electroporation was performed by suspending 1.0-3.0 ug of precipitated PCR product in 45 µl of electrocompetent cells and transferring the mixture to a 0.1 cm electroporation cuvette. The cuvette was then pulsed in a Bio-Rad Gene Pulser® II at 1.8 kV, 25° F., and 200Ω. The cells were then grown out in 1 ml 2YT (Difco) for 4 hours at 37° C. and the entire 1 ml was plated onto LB agar with 7.5 µg/ml spectinomycin and incubated at 37° C. for a period of 2-3 days.

Resultant spectinomycin resistant strains were cured of plasmid pKD46 as described in Datsenko and Wanner (2000), yielding strains s4480-182-1 (with the Ptac promoter driving asd (SEQ ID NO: 9)) and s4480-182-4 (with the Ptrc promoter driving Asd expression (SEQ ID NO: 10)).

Example 3

Example 3 demonstrates the utility of placing Ptac or Ptrc promoters upstream of asd for causing high expression levels of the asd gene product.

To asses the expression levels of Asd achieved by placing asd under the control of either Ptac or Ptrc, mutant strains were grown in shake flasks and assayed for Asd specific activity. Strains TH25.79, s4397-117-1, s4480-155-2, s4480-182-1, and s4480-182-4 (strains listed in Table 1) were grown in 20 ml media SM2 (24.36 µl $K_2HPO_4$, 9.52 g/l $KH_2PO_4$, 15 g/l yeast extract, 5 g/l $(NH_4)_2SO_4$, 32.5 g/l dextrose, 1.0 µl $MgSO_4-7H_2O$ pH 7.2) overnight on a New Brunswick G53 shaker at 240 rpm at 37° C. The resultant biomass was assayed for Asd specific activity by following the L-aspartate β-semialdehyde dependent reduction of $NADP^+$ as previously described (Cremer et al., 1988). As shown in Table 2, Asd activity is increased greatly by the introduction of either a Ptac promoter or a Ptrc promoter in front of the asd gene. Under these growth conditions, Asd specific activity ranges from 6.8 fold higher than wild-type (Ptrc with lac ribosome binding site) to 37.0 fold higher than wild-type (Ptac with asd ribosome binding site).

TABLE 2

Asd activity from various strains:

| Strain | Asd activity (nmol/min/mg) |
|---|---|
| TH25.79 | 239.4 |
| S4397-117-1 | 8865.6 |
| S4480-155-2 | 8364.5 |
| S4480-182-1 | 2662.8 |
| S4480-182-4 | 1635.5 |

Table 2. Asd enzyme specific activities of promoter-asd fusion strains when grown in media SM2. Each strain was assayed six times and averages are shown. Strains S4397-117-1, S4480-155-2, S4480-182-1, and S4480-182-4, were deposited on Mar. 1, 2005, at the National Center for Agricultural Utilization Research in Peoria, Ill. They were assigned deposit numbers NRRLB-30824, NRRLB-30825, NRRLB-30826, and NRRLB-30827, respectively.

Example 4

The following example illustrates that placing control of asd expression under the control of a Ptac promoter causes the expression of the asd gene product to become insensitive to the presence of amino acids in the growth media.

The wild-type promoter of asd is normally repressed in the presence of lysine, threonine and/or methionine (Haziza et al., 1982a). In order to test what effect amino acids have on the expression levels of Asd when the Ptac promoter is controlling asd expression, strains TH25.79 (wild-type asd promoter) and s4397-117-1 (including Ptac controlling asd expression (SEQ ID NO: 7)) were grown in the presence and absence of high levels of amino acid sources. Strains TH25.79 and s4397-117-1 (Table 1) were grown in 20 ml media BTC3 (1.0 g/l K2HPO4, 10.0 g/l (NH4)2SO4, 40.8 g/l Bis-Tris, 20 ml/l 50% solids corn steep liquor (Sigma), 25.0 g/l dextrose, and 1.2 g/l $MgSO4-7H_2O$ pH 7.0) with no supplementation, or with supplementation with either 1.0% casamino acids or with 1.5% yeast extract to an $OD_{600}$ of 7.0 in 250 ml baffled flasks on a New Brunswick G53 shaker at 240 rpm at 37° C. The resultant biomass was assayed for Asd specific activity by following the L-aspartate β-semialdehyde dependent reduction of $NADP^+$ as previously described (Cremer et al., 1988). As shown in Table 3, the wild-type promoter of TH25.79 is sensitive to the addition of amino acids, while the Ptac promoter of strain s4397-117-1 is insensitive. The presence of high levels of amino acids reduces the level of Asd in strain TH25.79 about 60%. Strain s4397-117-1 has no reduction in Asd levels when grown in the presence of high concentrations of amino acid sources.

TABLE 3

Asd activity in strains TH25.79 and s4397-117-1 (Ptac-asd) when supplemented with amino acid sources:
Asd activity (nmol/min/mg)

| Strain | No supplement | +1.0% CAA | +1.5% YE |
|---|---|---|---|
| TH25.79 | 1719.4 | 629.0 | 680.6 |
| S4397-117-1 | 6187.4 | 6411.6 | 7109.9 |

Table 3. Asd enzyme specific activities of strains TH25.79 (including wild-type promoter) and s4397-117-1 (including Ptac promoter with asd (SEQ ID NO: 7)) when grown with or without amino acid supplementation. Each strain was assayed six times and averages are shown.

Example 5

Example 5 discusses average performance of strain s4397-117-1 relative to strain TH25.79 in fermentors.

The average performance of strain s4397-117-1, relative to the parent strain TH25.79, was determined over a series of 69 fermentation runs with the test strain and 63 fermentation runs with the parent strain, where all runs were conducted in the same facility and in the same time period. Run specifications such as optical density, final product concentration, rate and yield are the averages for all runs with a particular strain.

Four 2000 mL shake flasks containing 500 mL of Medium A, were each inoculated with 1.6 mL of a culture that had previously been grown to an average optical density at 600 nm ($OD_{660}$) of 6.0 in Medium A, and then had been frozen in the presence of 10% glycerol. The flasks were shaken at 37 deg C. to an average $OD_{660}$ of 3.8. The flask cultures were used to inoculate a prepared seed fermentor containing an average of 5,724 Gal of sterilized medium B. The fermentor was operated at pH 6.9, 101 deg F., under aeration and agitation sufficient until the culture attained an average $OD_{660}$ of 14.9. The finished seed fermentor was used to inoculate a prepared final fermentor containing an average of 53,066 Gal of sterilized medium C. The fermentor was maintained at pH 6.9 and 90 deg F. at aeration and agitation rates that are typical for large-scale *E. coli*-based fermentations. The fermentors were operated in batch mode until the initial charge of dextrose was depleted, after which they were operated in fed-batch mode with dextrose solution as the feed. The fermentations were halted and the results were analyzed after an average of 42 hours of operation.

Strain s4397-117-1 showed, on average, a relative improvement of 2% higher in final product concentration, 10.8% higher in specific yield (measured as grams threonine produced per gram dextrose consumed), and 8% higher in product formation rate, relative to the average performance of the parent strain TH25.79.

TABLE 4

Culture Medium for Example 5

| Item | Medium A | Medium B | Medium C |
|---|---|---|---|
| Difco Tryptic Soy Broth | 30 g/L | | |
| Difco Yeast Extract | 5 g/L | | |
| Corn Steep Liquor CSL solids | | 10 g/L | 10 g/L |
| D-Glucose | | 93 g/L | 31 g/L |
| KH2PO4 | | 2.5 g/L | 2.5 g/L |
| MgSO4—7H2O | | 2.0 g/L | 2.0 g/L |
| Citric acid | | ≦0.5 g/L | ≦0.5 g/L |
| NH4SO4 | | ≦0.5 g/L | ≦0.5 g/L |
| MnSO4—H2O | | ≦0.5 g/L | ≦0.5 g/L |
| FeSO4—7H2O | | ≦0.5 g/L | ≦0.5 g/L |

Example 6

Construction of Plasmid p4202-133-1

A. Isolation, Purification, and Enzymatic Digestion of the Plasmid pUC19

The plasmid pUC19 (GenBank Accession #M77789), which carries the ampicillin antibiotic resistance gene, was used as the source for the replication origin functional in *E. coli*. The pUC19 was prepared from *E. coli* cells that were grown on Luria Broth (10 µl tryptone, 5 g/l yeast extract, 5 g/l NaCl) with 100 ug/ml ampicillin. The plasmid was isolated by alkaline method (H. C. Birnboim and J. Doly, *Nucleic Acids Res.*, 7:1513-1523 (1979)). Approximately 1 µg of pUC19 was digested with BamHI and EcoRI to completion. The digest was phenol:chloroform:isoamyl extracted, then precipitated with three volumes of ethanol and 1/10 volume of 5M Na acetate. It was re-suspended in 20 µl of sterile double-distilled water (ddH$_2$O).

B. Polymerase Chain Reaction and Preparation of the Constitutive Ptac-Like Promoter::asd PCR Product.

The Polymerase Chain Reaction (PCR) was done using Invitrogen Corporation's Platinum Pfx DNA Polymerase (Carlsburg, Calif.). The following was added to an autoclaved microcentrifuge tube on ice: 5 µl 10×Pfx Amplification Buffer, 1.5 µl 10 mM dNTPs mixture, 1 µl 50 mM MgSO4, 0.75 µl 50 µM tac-asd-for (SEQ ID NO: 14) (FIG. 6), 0.75 µl 50 µM tac-asd-rev (SEQ ID NO: 15) (FIG. 6), 1 µl chromosomal DNA from *Escherichia coli* TH25.79 (~50 ng), 1 µl Platinum Pfx DNA polymerase, and 39 µl of sterile ddH$_2$O. The tube was capped and centrifuged briefly in an Eppendorf microcentrifuge (Hamburg, Germany) to collect content at the bottom of the tube. PerkinElmer Applied Biosystem's GeneAmp PCR system 9700 (Foster City, Calif.) was the thermal cycler used. A hot start was used at 94° C. for 2 minutes. The PCR was performed by having 35 cycles of the PCR amplification: the denaturant was at 94° C. for 30 seconds, the annealing was done at 50° C. for 30 seconds, and the extension was done at 72° C. for 2 minutes.

The constitutive Ptac-like promoter::asd PCR product was phenol:chloroform:isoamyl extracted. It was digested with BamHI and EcoRI to completion. The constitutive Ptac-like promoter::asd was again extracted with phenol:chloroform:isoamyl, then it was precipitated with 3 volumes of ethanol and 1/10 volume of 5M Na acetate. It was re-suspended in 10 µl of sterile ddH$_2$O.

C. Ligating and Transforming of p4202-133-1 into Strain *Escherichia coli* TH25.79

The constitutive Ptac-like promoter::asd PCR product contained one restriction site each for endonucleases HinDIII and PvuI. A ligation was done to construct the plasmid p4202-133-1. Promega (Madison, Wis.) T4 DNA ligase was used in this procedure. 1 µl pUC19 digested with BamHI and EcoRI, 311 Ptac::asd PCR product digested with BamHI and EcoRI, 1 µl of Ligase Buffer, 1 µl of Promega T4 DNA Ligase, and 4 µl of nuclease-free H$_2$O were mixed together in a sterile microcentrifuge tube, spun down briefly in Eppendorf microcentrifuge (Hamburg, Germany) at room temperature, and allowed to sit overnight at room temperature. The ligation mixture was transformed into *Escherichia coli* MCR. The plasmid was then isolated and purified and then transform into *Escherichia coli* TH25.79. The p4202-133-1 was isolated and purified and then digested with HinDIII and PvuI to completion, separately.

A strain of TH25.79 bearing plasmid p4202-133-1 was deposited on Mar. 1, 2005, at the National Center for Agricultural Utilization Research in Peoria, Ill. It was assigned deposit number NRRL B-30823. The plasmid includes a constitutive Ptac-like promoter (SEQ ID NO: 16). The plasmid further includes a constitutive Ptac-like promoter with an asd binding site operably associated with an asd gene.

Example 8

Insensitivity of the Constitutive Ptac-Like Promoter::asd Strain to Repression by 10 mM Lysine The following example illustrates that placing control of asd expression under the control of a constitutive Ptac-like promoter caused the expression of the asd gene product to become insensitive to the presence of lysine in the Davis Minimal Medium (per 1 liter 7.0 g dipotassium phosphate, 2.0 g monopotassium phospate, 0.5 g/l sodium citrate, 0.1 magnesium sulfate, 1.0 g ammonium sulfate, pH 7.0 supplemented with 0.2% (w/v) dextrose).

The wild-type promoter of asd is normally repressed in the presence of lysine, threonine and/or methionine (Haziza et al., 1982a). To test what effect lysine has on the expression levels of Asd when the constitutive Ptac-like promoter is controlling asd expression, strains TH25.79 (wild-type asd promoter) and TH25.79 p4202-133-1 (Constitutive Ptac-like promoter controlling asd expression with RBS from asd (SEQ ID NO: 16)) were grown in the presence and absence of 10 mM lysine. Strains TH25.79 and TH25.79 p4202-133-1 (Table 5) were grown in 20 ml Davis Minimal medium with no supplementation, or with supplementation 10 mM lysine to an OD$_{600}$ of ~0.7 in 250 ml baffled flasks on a New Brunswick G53 shaker at 240 rpm at 37° C. The resultant biomass was assayed for Asd specific activity by following the L-aspartate β-semialdehyde dependent reduction of NADP$^+$ as previously described (Cremer et al., 1988). As shown in Table 5, the wild-type promoter of TH25.79 is sensitive to the addition of 10 mM lysine, while the promoter on the plasmid p4202-133-1 is insensitive.

TABLE 5

| Strain | No Supplement | 10 mM lysine |
|---|---|---|
| TH25.79 | 2317 | 881 |
| TH25.79 p4202-133-1 | 5996 | 5307 |

Table 5. Asd enzyme specific activities of *Escherichia coli* TH25.79 (wild-type promoter) and strain TH25.79 p4202-133-1 (promoter) when grown with or without 10 mM lysine supplementation. Each strain was assayed three times and averages are shown. Results express Asd enzyme specific activity in units of nmol/min/mg protein.

Example 9

Average Performance of *Escherichia coli* TH25.79 to *Escherichia coli* TH25.79 p4204-133-1

The average performance of *Escherichia coli* TH25.79 p4204-133-1, relative to the parent strain TH25.79, was determined in shake flasks. A total of 5 shake flasks were done for each strain.

Frozen cultures of strain TH25.79 and TH25.79 p4202-133-1 were seeded into separate 10 ml test tubes of Luria Broth media and allowed to incubate overnight at 37° C., 240 rpm, on a New Brunswick G53 shaker. A 2% (v/v) seed of each culture was added to 20 ml of Luria Broth in a 125 ml baffled flask and allowed to incubate 24 hours at 37° C. while New Brunswick G53 shaker at 240 rpm. Again, a 2% (v/v) volume of each culture was seeded into 20 ml FM7 media in a 125 ml baffled flask (Table 6) and allowed to shake for 48 hours at 37° C., 240 rpm, on a New Brunswick G53 shaker. Samples were taken to determine the yield and titer of threonine (g/l). The results are shown in Table 7.

TABLE 6

| Solution A | |
|---|---|
| $H_2O$ | 680 ml |
| Citric acid | 2 g |
| $(NH_4)_2SO_4$ | 25 g |
| $KH_2PO_4$ | 7.46 g |
| Trace metal solution | 2 ml |
| $CaCO_3$ (reagent grade) | 20 g |
| pH (KOH or HCl) | 7.2 g |
| $H_2O$ (bring volume to) | 750 ml |
| Dispense 15 ml/flask | |
| Solution B | |
| Dextrose (plant grade) | 48 g |
| $MgSO_4 \cdot 7H_2O$ | 2.4 g |
| $H_2O$ (bring volume to) | 300 ml |
| Trace metal solution | |
| $Na_2SO_4$ | 1 g |
| $MnSO_4$ | 0.2 g |
| $ZnCl_2$ | 0.2 g |
| $CoCl_2 \cdot 6H_2O$ | 0.2 g |
| $CuSO_4 \cdot 5H_2O$ | 0.03 g |
| $FeSO_4 \cdot 7H_2O$ | 3.75 g |
| HCl | 0.8 g |
| $H_2O$ | 100 ml |

Table 6. FM7 medium recipe. Solution A and B should be autoclaved, and then dispense 5 ml of Solution B to flasks containing Solution A. Trace mineral solution should be filtered through a pore size of 0.2 µM.

TABLE 7

| Strain | Yield | Titer |
|---|---|---|
| TH25.79 | 13.8 | 4.2 |
| TH25.79 p4202-133-1 | 22.1 | 6.7 |

Table 7. Yield and titer comparison of *Escherichia coli* TH25.79 and strain TH25.79 p4202-133-1. Yield equals the total threonine produced divided by the total dextrose consumed times 100. Titer equals the final threonine concentration (g/l).

Patents, patent applications, publications, scientific articles, books, web sites, and other documents and materials referenced or mentioned herein are indicative of the levels of skill of those skilled in the art to which the inventions pertain, as of the date each publication was written, and all are incorporated by reference as if fully rewritten herein. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above including but not limited to any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing or optionally allowing the removal of any subject matter from the genus, regardless of whether or not the excised materials or options were specifically recited or identified in haec verba herein, and all such variations form a part of the original written description of the inventions. In addition, where features or aspects of an invention are described in terms of a Markush group, the invention shall be understood thereby to be described in terms of each and every, and any, individual member or subgroup of members of the Markush group.

The inventions illustratively described and claimed herein can suitably be practiced in the absence of any element or elements, limitation or limitations, not specifically disclosed herein or described herein as essential. Thus, for example, the terms "comprising," "including," "containing," "for example", etc., shall be read expansively and without limitation. In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement was specifically and without qualification or reservation expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:
1. The isolated plasmid p4202-133-1.
2. An *Escherichia coli* host cell deposited as NRRLB-20823.

* * * * *